United States Patent [19]
Schneider

[11] Patent Number: 6,073,043
[45] Date of Patent: Jun. 6, 2000

[54] MEASURING POSITION AND ORIENTATION USING MAGNETIC FIELDS

[75] Inventor: Mark Schneider, Williston, Vt.

[73] Assignee: CorMedica Corporation, Natick, Mass.

[21] Appl. No.: 08/996,125

[22] Filed: Dec. 22, 1997

[51] Int. Cl.[7] .................................................. A61B 5/05
[52] U.S. Cl. ..................... 600/424; 128/899; 324/207.11
[58] Field of Search ..................... 600/424, 439, 600/407, 373, 374; 128/899; 606/10, 15; 324/207.11, 207.13–207.21, 260

[56] References Cited

U.S. PATENT DOCUMENTS

| | | |
|---|---|---|
| 4,054,881 | 10/1977 | Raab . |
| 4,287,809 | 9/1981 | Egli et al. . |
| 4,314,251 | 2/1982 | Raab . |
| 4,328,548 | 5/1982 | Crow et al. . |
| 4,346,384 | 8/1982 | Raab . |
| 4,394,831 | 7/1983 | Egli et al. . |
| 4,396,885 | 8/1983 | Constant . |
| 4,613,866 | 9/1986 | Blood . |
| 4,622,644 | 11/1986 | Hansen . |
| 4,710,708 | 12/1987 | Rorden et al. . |
| 4,737,794 | 4/1988 | Jones . |
| 4,742,356 | 5/1988 | Kuipers . |
| 4,849,692 | 7/1989 | Blood . |
| 4,945,305 | 7/1990 | Blood . |
| 5,172,056 | 12/1992 | Voisin . |
| 5,307,072 | 4/1994 | Jones, Jr. . |
| 5,377,678 | 1/1995 | Dumoulin et al. . |
| 5,425,367 | 6/1995 | Shapiro et al. . |
| 5,453,686 | 9/1995 | Anderson . |
| 5,558,091 | 9/1996 | Acker et al. . |
| 5,592,939 | 1/1997 | Martinelli . |
| 5,622,169 | 4/1997 | Golden et al. . |
| 5,729,129 | 3/1998 | Acker . |
| 5,752,513 | 5/1998 | Acker et al. . |
| 5,762,064 | 6/1998 | Polvani . |
| 5,769,843 | 6/1998 | Abela et al. . |
| 5,782,765 | 7/1998 | Jonkman . |
| 5,824,005 | 10/1998 | Motamedi et al. . |
| 5,830,210 | 11/1998 | Rudko et al. . |

FOREIGN PATENT DOCUMENTS 0 655 138 B1   4/1998   European Pat. Off. .

*Primary Examiner*—Marvin M. Lateef
*Assistant Examiner*—Shawna J Shaw
*Attorney, Agent, or Firm*—Miles & Stockbridge P.C.; William L. Feeney

[57] ABSTRACT

A method and apparatus for determining the position and orientation of a remote object relative to a reference coordinate frame includes a plurality of field-generating elements for generating electromagnetic fields, a drive for applying, to the generating elements, signals that generate a plurality of electromagnetic fields that are distinguishable from one another, a remote sensor having one or more field-sensing elements for sensing the fields generated and a processor for processing the outputs of the sensing element(s) into remote object position and orientation relative to the generating element reference coordinate frame. The position and orientation solution is based on the exact formulation of the magnetic field coupling as opposed to approximations used elsewhere. The system can be used for locating the end of a catheter or endoscope, digitizing objects for computer databases, virtual reality and motion tracking. The methods presented here can also be applied to other magnetic tracking technologies as a final "polishing" stage to improve the accuracy of their P&O solution.

30 Claims, 15 Drawing Sheets

EXPLODED VIEW OF 2
FLEXIBLE PRINTED CIRCUIT
BOARD LAYERS

MEASURING POSITION AND ORIENTATION USING MAGNETIC FIELDS

BACKGROUND OF THE INVENTION

The present invention relates to a system and method for determining the position and orientation of a remote object relative to a reference coordinate frame using magnetic fields. More specifically, the position and orientation of a medical device, such as a catheter, within a patient is determined.

Various magnetic tracking systems use circular loop antennas for magnetic field generation and detection. One or more coils generate distinguishable magnetic fields and one or more coils detect the generated magnetic fields. Knowing the position, orientation and geometry of the generating coils and the signal sensed in response to the magnetic field generation, the position and orientation of the sensing coils can be determined with respect to the field generators. The magnetic field generators usually establish the coordinate reference frame from which measured position and orientation is referenced. Depending on the number of coils used for generation and sensing, measurement of values for up to 6 degrees of freedom (three position values and three orientation values) of an object can be obtained. The equations normally used for calculating position and/or orientation using a generated magnetic field are almost all based on the assumption that the distance between the generating and detecting coils (r) is larger than the radius (a) of the generating coil. This equation is known as the infinitesimal dipole model. This assumption is explicitly used in the following U.S. patents, hereby incorporated by reference.

Hansen (U.S. Pat. No. 4,622,644) discloses a 5 degree-of-freedom (5DOF) position and orientation (P&O) measurement system that uses 2 or 3 sets of orthogonal Hall effect sensors and a bar magnet for generating a magnetic field. It is noted that using 2 sets of 3-axis orthogonal Hall effect sensors restricts the region of operation due to ambiguities. A noise error vector is noted that contains the estimated residual noise measured at the sensors. His method of solution starts by determining an approximate starting point for a calculation process that solves the system of 9 non-linear equations in 5 unknowns (x position, y position, z position, bar magnet azimuth, bar magnet elevation). The non-linear equations are based on the B-field approximation. Likewise, Hansen (U.S. Pat. No. 4,642,786) uses the same P&O solution approach in a variety of tracking system configurations (both 5DOF and 6DOF) using the retransmission of magnetic fields.

Rorden et al. (U.S. Pat. No. 4,710,708) discloses locating methods using various generating and detecting coils for underground surveying. These include 2, 3, or more, 3-axis orthogonal detecting (sensing) coil sets with a single transmitting coil; a 2-axis orthogonal generating coil set with a 3-axis orthogonal detecting set; a plurality of single axis collinear generating coils with a three axis orthogonal detecting set, among others. It is noted that at least 6 coil elements are required to avoid ambiguities or additional information must be utilized. Also noted is that using 2 sets of 3 axis orthogonal detecting sets restricts the region of operation due to ambiguities. The method of solution utilizes a process that solves the system of 6 non-linear equations in 6 unknowns (x position, y position, and z position, x direction cosine, y direction cosine, and z direction cosine). The direction cosines are composed of trigonometric combinations of azimuth and elevation such that this set of equations can be reduced to 5 unknowns. The non-linear equations are based on the B-field approximation.

Bladen et al. (WO 94/04938) discloses two system configurations: 3 3-axis orthogonal generating coil sets with a single axis detecting coil (5DOF) and one 3-axis orthogonal generating coil set with a 3-axis orthogonal detecting coil set (6DOF). Bladen's Appendix A describes the approximate B-field equations utilized in their process. Like Hansen, the 5DOF method of solution starts by determining an approximate starting point for the process and then solves a system of 9 non-linear equations in 5 unknowns (x position, y position, z position, azimuth and elevation).

Dumoulin et al. (U.S. Pat. No. 5,377,678) starts with equations that are remarkably similar to Rorden's equations (again, B-field approximations). He never mentions the magnetic moment (m) from Rordens equations and has a 5DOF system with 5 receiver coils and a single axis generating coil. He solves 5 non-linear equations in 5 unknowns (x position, y position, z position, azimuth and elevation) and notes that there must be at least 5 coil elements. To start the process he places the generator coil at a known position and orientation. As an aside, he first states that two transmitter coils are needed to determine both position and orientation (column 2, lines 66 on) and then states he needs one transmit coil to determine position and orientation (column 4, lines 41 on).

While it may not be obvious, a number of other patents use the infinitesimal dipole approximation, including Jones (U.S. Pat. Nos. 4,737,794, 5,307,072), Raab (U.S. Pat. Nos. 4,054,881, 4,314,251, 4,346,384), Crow et al. (U.S. Pat. No. 4,328,548), Egli et al. (U.S. Pat. Nos. 4,287,809, 4,394,831), Constant (U.S. Pat. No. 4,396,885), Blood (U.S. Pat. No. 4,613,866) and Kuipers (U.S. Pat. No. 4,742,356).

Published PCT application WO 97/32179 to Acker discloses a location system wherein at least one field generating coil or device creates different electromagnetic fields during different time intervals. This system specifically covers pulsed-DC field generation and excitation control. It also describes a non-linear equation solution to the tracking problem, which has already been covered by others.

A few patents note needed corrections when using the infinitesimal dipole model to make it more accurate when working close to the generating coil. Jones (U.S. Pat. No. 4,737,794) builds upon the dipole model and discloses a quasi-closed form (non-iterative) matrix solution of P&O using one 3-axis orthogonal generating coil set with a 3-axis orthogonal detecting coil set (6DOF). As noted above, Jones starts with the dipole approximation. He then introduces additional correction terms from an infinite series of Legendre polynomials with the unstated proviso that the distance between the generating and receiving coils (r) is greater that the transmitting coil radius (a). These correction terms are calculated based on the previous P&O solution. He casually mentions that elliptic integrals can also be used for generating these correction terms to the dipole model.

Jones (U.S. Pat. No. 5,307,072) discloses methods for compensating for positional offsets of generating coil and sensing coil sets. These methods are deeply embedded into his P&O process disclosed in 4,737,794. As noted above, Jones starts with the dipole approximation. He then introduces additional correction terms from an infinite series of Legendre polynomials, again with the unstated proviso that r>a that correct for coil size, geometry and coil placement. These correction terms are calculated based on the previous P&O solution but can be used directly. The use of elliptic integrals, hypergeometric functions, etc. is also mentioned as a means of generating these correction terms to the dipole model. The methods detailed in both Jones patents will yield incorrect results when r<a. Neither will work at all when r=0 (the sensor coil collocated within the generating coil).

Extending these concepts further, certain patents address generating coils of any shape. They also require the use of non-linear equation solving to provide part or all of their position and orientation solution. Ben-Haim et al. (WO 96/05768) discloses a position and orientation measurement system that uses any shape generating coils. He too uses Legendre polynomials to define the magnetic field structure, correct for r>a only. He claims as new to the art non-concentric sensing coils for his 6DOF approach but Jones (U.S. Pat. No. 5,307,072) has already addressed this issue.

Blood (U.S. Pat. No. 5,600,330) discloses a system to determine P&O using 2 or 3 non-dipole generating antennas (e.g., rectangular coils) that are not necessarily orthogonal. It does use a 3 axis orthogonal detecting coil set and yields a 6DOF solution. The distortion immunity and large volume of measurement space are obtained by constraining the sensing device to work within the perimeters of the generating coils. It is noted that a process that iteratively determines P&O could have been developed. It is also noted that the number of receiving antenna (i) times the number of transmitting antenna (j) must equal at least 6 with the requirement that i and j must at least be two (for 6DOF). It is noted that the location, orientation and geometry of the coils must be known, implying that the B-field equations can be explicitly stated. A non-linear process solving 6 equations in 3 unknowns (x position, y position and z position) based on measured magnitudes and vector dot products is developed. An exact non-iterative process is then used to compute orientation. Bloods process eliminates the need to compute elliptic integrals or Legendre polynomials but only works well within the confines of the generating coils.

Other patents that use non-dipole fields in very different ways include Acker et al. (U.S. Pat. No. 5,558,091), Martinelli (U.S. Pat. No. 5,592,939) and Voisin (U.S. Pat. No. 5,172,056). These disclosures use multiple coils to form fields that are not dipole in nature but vary quasi-linearly in certain respects.

OBJECTS AND SUMMARY OF THE INVENTION

Accordingly, it is a primary object of the present invention to provide a new and improved position and orientation (P&O) system allowing determination of the position and orientation of a remote device.

A more specific object of the present invention is to provide a new and improved medical system.

A further object of the present invention is to provide a laser catheter with precise position determination.

Yet another object of the present invention is to provide a catheter having position determination without requiring multiple bulky structures in the catheter.

A further object of the present invention is to provide catheter position determination without placing constraints on the relative positions of the catheter and an external locating system.

Yet another object of the present invention is to provide a catheter for percutaneous myocardial revascularization.

The above and other features of the present invention which will be more readily understood when the following detailed description is considered in conjunction with the accompanying drawings are realized by a medical system for treating a patient. Pluralities of transducers are operable to determine the location of a medical device in a patient, the transducers including one or more device transducers and one or more external transducers. A medical device is insertable into a patient, the medical device having the one or more device transducers. An external locator is operable outside and adjacent to the patient, the external locator having the one or more external transducers. The system sequentially energizes one or more of the device transducers and/or the external transducers. Sensed signals are generated from one or more of the transducers, each sensed signal from a given one of the transducers depending on the energizing of another of the transducers. A processor is responsive to the sensed signals, the processor determining at least two location parameters of the medical device in the patient using a plurality of equations, which equations do not require a minimum separation distance from the energized transducer to the transducer generating the sensor signal for validity. As used herein, location parameters shall include position and orientation information relative to the catheter (or other remote device).

The present invention may alternately be described as a method of determining the location of a remote device comprising the steps of: using a system having a plurality of transducers operable to determine the location of a remote device, the transducers including one or more device transducers and one or more locator transducers; placing the remote device in an operation zone, the remote device having the one or more device transducers; placing a locator away from, but within an interaction distance from, the remote device, the locator having the one or more locator transducers; sequentially energizing one or more of the device transducers and/or the locator transducers; generating sensed signals from one or more of the transducers, each sensed signal on a given one of the transducers depending on the energizing of another of the transducers; and supplying the sensed signals to a processor, the processor determining at least two location parameters of the remote device using a plurality of equations, which equations do not require a minimum separation distance from the energized transducer to the transducer generating the sensor signal for validity; and wherein the system is a medical system used to treat a patient, the remote device is a medical device and the operation zone is within a patient.

The present invention may alternately be described as a method of determining the location of a remote device comprising the steps of: using a system having a plurality of transducers operable to determine the location of a remote device, the transducers including one or more device transducers and one or more locator transducers; placing the remote device in an operation zone, the remote device having the one or more device transducers; placing a locator away from, but within an interaction distance from, the remote device, the locator having the one or more locator transducers; sequentially energizing one or more of the device transducers and/or the locator transducers; generating sensed signals from one or more of the transducers, each sensed signal on a given one of the transducers depending on the energizing of another of the transducers; and supplying the sensed signals to a processor, the processor determining at least two location parameters of the remote device using a plurality of equations, which equations do not require a minimum separation distance from the energized transducer to the transducer generating the sensor signal for validity; and wherein each of the transducers generates and/or senses an electromagnetic field.

BRIEF DESCRIPTION OF THE DRAWINGS

The above and other features of the present invention will be more readily understood when the following detailed description is considered in conjunction with the accompanying drawings wherein like characters represent like parts throughout the several views and in which.

DETAILED DESCRIPTION

A number of magnetic position and orientation determining system configurations using magnetic fields are presented. The methods determine the relative position and orientation of a sensing device with respect to a generator of magnetic fields which establishes the reference coordinate frame. The sensing devices can be one, two or three-axis magnetic sensing elements such as coils of wire, Hall-effect sensors, magnetometers and/or any sensors based on magnetoresistive, magnetoinductive, or galvanomagnetic technology. The field generating devices can be one, two or three-axis coils of wire or magnets. All configurations can be reversed using the principal of reciprocity; i.e., the sensing and generating elements can be interchanged. The systems can utilize AC waveforms or pulsed-DC waveforms or retransmitted waveforms. Time, frequency, phase or various combinations of each can be utilized to distinguish between the various excitations of the generating elements. The process can also be used to improve the solutions of other tracking systems that are based on approximate B-field formulations.

All the configurations calculate the position and orientation solution based on the exact formulation of the near field (or quasi-static) magnetic field coupling as opposed to approximations used elsewhere. Of course, a P&O process utilizing equations for the far field (radiation) magnetic field could also be solved. Generating coil position can be included in the equation by making substitution of the form:

$x' = x - x0$ $y' = y - y0$ $z' = z - z0$ where x', y' and z' are the translated positions from the true x, y and z coordinate system with offsets x0, y0 and z0.

Generating coil orientation can be included in the equations by multiplying a 1×3 B-field vector with a 3×3-rotation matrix.

The process utilizes the known position, orientation and geometry of the generating elements, their effective areas, driver gains, preamplifier gains, sensor effective areas and other system constants. The effective area for a coil is the area of a single coil turn times the number of turns. This calibration data is gathered during the manufacturing process and is applied in real time during execution of the P&O process.

Two examples of exact B-field equations are:

Circular Coil of Wire

Figure 1:
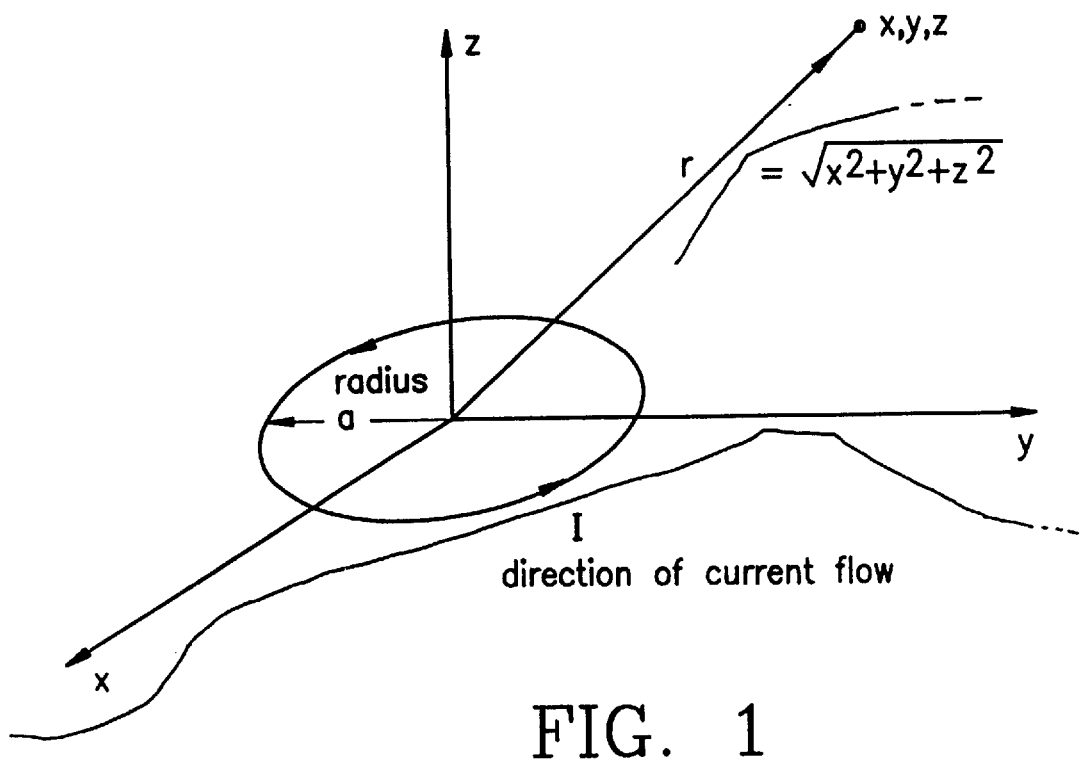
FIGS. 1–5 are simplified xyz schematic diagrams for explaining the derivation of various equations and configurations used with the present invention.

Coil in the x-y plane (FIG. 1):

$$\vec{B}_x = \frac{\lambda \mu_0 I}{2\pi} \frac{xz}{(x^2+y^2)\sqrt{\left(a+\sqrt{x^2+y^2}\right)^2+z^2}} \left(-K(\alpha)+E(\alpha)a^2+x^2+y^2+\frac{z^2}{\left(a-\sqrt{x^2+y^2}\right)^2+z^2}\right) \quad (1)$$

$$\vec{B}_y = \frac{\lambda \mu_0 I}{2\pi} \frac{yz}{(x^2+y^2)\sqrt{\left(a+\sqrt{x^2+y^2}\right)^2+z^2}} \left(-K(\alpha)+E(\alpha)a^2+x^2+y^2+\frac{z^2}{\left(a-\sqrt{x^2+y^2}\right)^2+z^2}\right) \quad (2)$$

$$\vec{B}_z = \frac{\lambda \mu_0 I}{2\pi} \frac{1}{\sqrt{\left(a+\sqrt{x^2+y^2}\right)^2+z^2}} \left(K(\alpha)+E(\alpha)a^2-x^2-y^2-\frac{z^2}{\left(a-\sqrt{x^2+y^2}\right)^2+z^2}\right) \quad (3)$$

where: $K(\alpha) = \int_0^{\frac{R}{2}} \frac{d\theta}{\sqrt{(1-\alpha^2 \sin^2\theta)}}$ (4)

$E(\alpha) = \int_0^{\frac{R}{2}} \sqrt{(1-\alpha^2 \sin^2\theta)}\, d\theta$ (5)

$\alpha = \sqrt{\frac{4ar}{(a+r)^2+z^2}}$ (6)

$\mu_0$ is the permeability of free space; a is the coil radius; I is the current flowing through the coil and λ represents the number of turns comprising the coil. Equations for coils in the x-z plane and y-z plane can be obtained from the above by the use of obvious substitutions or by using a 3×3 rotation matrix.

Rectangular Coil of Wire

Coil in the x-y plane (FIG. 2):

$$\vec{B}_x = \frac{\lambda\mu_0 I}{\pi}(-b+2y)\frac{z}{\sqrt{4x^2-4xa+4y^2+a^2+b^2+4z^2-4yb}\,(4x^2-4xa+a^2+4z^2)} - \quad (7)$$

$$\frac{\lambda\mu_0 I}{\pi}(b+2y)\frac{z}{\sqrt{4x^2-4xa+4y^2+a^2+b^2+4z^2+4yb}\,(4x^2-4xa+a^2+4z^2)} -$$

$$\frac{\lambda\mu_0 I}{\pi}(-b+2y)\frac{z}{\sqrt{4x^2+4xa+4y^2+a^2+b^2+4z^2-4yb}\,(4x^2+4xa+a^2+4z^2)} +$$

$$\frac{\lambda\mu_0 I}{\pi}(b+2y)\frac{z}{\sqrt{4x^2+4xa+4y^2+a^2+b^2+4z^2+4yb}\,(4x^2+4xa+a^2+4z^2)}$$

$$\vec{B}_y = \frac{\lambda\mu_0 I}{\pi}(a+2x)\frac{z}{\sqrt{4x^2+4xa+4y^2+a^2+b^2+4z^2+4yb}\,(4y^2+4yb+b^2+4z^2)} - \quad (8)$$

$$\frac{\lambda\mu_0 I}{\pi}(a+2x)\frac{z}{\sqrt{4x^2+4xa+4y^2+a^2+b^2+4z^2-4yb}\,(4y^2-4yb+b^2+4z^2)} +$$

$$\frac{\lambda\mu_0 I}{\pi}(a-2x)\frac{z}{\sqrt{4x^2-4xa+4y^2+a^2+b^2+4z^2+4yb}\,(4y^2+4yb+b^2+4z^2)} -$$

$$\frac{\lambda\mu_0 I}{\pi}(a-2x)\frac{z}{\sqrt{4x^2-4xa+4y^2+a^2+b^2+4z^2-4yb}\,(4y^2-4yb+b^2+4z^2)}$$

$$\vec{B}_z = \frac{\lambda\mu_0 I}{\pi}(a-2x)\frac{\left(y-\frac{b}{2}\right)}{\sqrt{4x^2-4xa+4y^2+a^2+b^2+4z^2-4yb}\,(4y^2-4yb+b^2+4z^2)} + \quad (9)$$

$$\frac{\lambda\mu_0 I}{\pi}(a+2x)\frac{\left(y-\frac{b}{2}\right)}{\sqrt{4x^2+4xa+4y^2+a^2+b^2+4z^2-4yb}\,(4y^2-4yb+b^2+4z^2)} -$$

$$\frac{\lambda\mu_0 I}{\pi}(a-2x)\frac{\left(y+\frac{b}{2}\right)}{\sqrt{4x^2-4xa+4y^2+a^2+b^2+4z^2+4yb}\,(4y^2+4yb+b^2+4z^2)} -$$

$$\frac{\lambda\mu_0 I}{\pi}(a+2x)\frac{\left(y+\frac{b}{2}\right)}{\sqrt{4x^2+4xa+4y^2+a^2+b^2+4z^2+4yb}\,(4y^2+4yb+b^2+4z^2)} -$$

$$\frac{\lambda\mu_0 I}{\pi}(-b+2y)\frac{\left(-x-\frac{a}{2}\right)}{\sqrt{4x^2+4xa+4y^2+a^2+b^2+4z^2-4yb}\,(4x^2+4xa+a^2+4z^2)} -$$

$$\frac{\lambda\mu_0 I}{\pi}(b+2y)\frac{\left(-x+\frac{a}{2}\right)}{\sqrt{4x^2-4xa+4y^2+a^2+b^2+4z^2+4yb}\,(4x^2-4xa+a^2+4z^2)} +$$

$$\frac{\lambda\mu_0 I}{\pi}(-b+2y)\frac{\left(-x+\frac{a}{2}\right)}{\sqrt{4x^2-4xa+4y^2+a^2+b^2+4z^2-4yb}\,(4x^2-4xa+a^2+4z^2)} +$$

$$\frac{\lambda\mu_0 I}{\pi}(b+2y)\frac{\left(-x-\frac{a}{2}\right)}{\sqrt{4x^2+4xa+4y^2+a^2+b^2+4z^2+4yb}\,(4x^2+4xa+a^2+4z^2)}$$

$\mu_0$ is the permeability of free space; a is the length of the loop in the x direction; b is the length of the loop in the y direction; I is the current flowing through the coil and $\lambda$ represents the number of turns comprising the coil. Equations for coils in the x-z plane and y-z plane can be obtained from the above by the use of obvious substitutions or by using a 3×3 rotation matrix.

Any means of generating a B-field that can be explicitly stated in mathematical terms can be utilized in this patent. It should also be noted that mathematical approximations to the B-field will work, but only with as much accuracy as the approximation allows, e.g., an approximation based on the infinitesimal dipole only works for r>>a. Some of these approaches are already patented.

Some words about the rectangular vs. circular coils are in order. The evaluation of magnetic field generated by rectangular coils need not be expressed in terms of elliptic integrals. While the exact form of the B-field for rectangular coils appears foreboding, the elimination of the need for calculating the values of the elliptic integrals may in fact be a plus. (Elliptic integral evaluation is usually based on rational function approximations or other methods that take extra time to compute.) This is especially true if the Jacobian (or Hessian) needs to be calculated (see following section). Exact calculation of the Jacobian and/or Hessian can be accomplished using symbolic software. The Jacobian and Hessian for the circular coils, however, require further evaluations of the elliptic integrals.

While it is not my intent to teach others about solving non-linear systems of equations or least squares (optimization) problems, a few words are in order. There are two types of non-linear equation problems, the non-linear systems of equations problem and the non-linear least squares problem. The non-linear systems of equations problem is: given n functions $f_1, f_2 \ldots, f_n$ of the n variables $x_1, x_2 \ldots, x_n$ find values for $x_1, x_2 \ldots, x_n$ that solve the non-linear system of $$f_i(x_1, x_2 \ldots, x_n) = 0, \; 1 \leq i \leq n$$

The non-linear least squares problem is: given m functions $f_1, f_2, \ldots f_m$ of the n variables $x_1, x_2 \ldots, x_n$, with $m \geq n$, find values for $x_1, x_2 \ldots, x_n$ that solve the non-linear least squares problem $$+ \frac{\lambda \mu_0 I}{\pi} \frac{(b+2y)\left(-x-\frac{a}{2}\right)}{\sqrt{4x^2 + 4xa + 4y^2 + a^2 + b^2 + 4z^2 + 4yb} \, (4x^2 + 4xa + a^2 + 4z^2)} \quad (9)$$

Many methods exist to tackling these problems with the predominant methods requiring the evaluation of the Jacobian (a matrix of partial derivatives of the equations with respect to the unknowns), either explicitly or by finite differences and sometimes requiring the evaluation of the Hessian (a matrix of second partial derivatives of the equations with respect to the unknowns). These methods are often referred to as Newton methods, gradient methods or steepest descent methods or variations on that theme.

Good introductions to these methods and basic processes are found in, inter alia:

Dennis Jr., J. E., Schnabel, Robert B. "Numerical Methods for Unconstrained Optimization and Nonlinear Equations." Prentice-Hall, Inc., 1983.

More, Jorge J., Garbow, Burton S., Hillstrom, Kenneth E. "User Guide For MINPACK-1." Argonne National Laboratory, August 1980.

Press, William H., Teukolsky, Saul A., Vetterling, William T., Flannery, Brian P. "Numerical Recipes in FORTRAN, The Art of Scientific Computing, Second Edition." Cambridge University Press, 1992.

More advanced versions of these methods are in:

Dennis Jr., John E., Gay, David M., Welsch, Roy E. "ALGORITHM 573, NL2SOL-An Adaptive Nonlinear Least-Squares Algorithm." ACM Transactions on Mathematical Software, Vol. 7, No. 3, September 1981, pages 369–383.

More, Jorge J., Cosnard, Michel Y. "ALGORITHM 554, BRENTM, A Fortran Subroutine for the Numerical Solution of Systems of Nonlinear Equations." ACM Transactions on Mathematical Software, Vol. 6, No. 2, June 1980, pages 240–251.

Schnabel, Robert B., Frank, Paul D. "Tensor Methods for Nonlinear Equations." SIAM Journal on Numerical Analysis, Vol. 21 No. 5, October 1984, pages 815–843.

Because these methods are iterative there is no guarantee that they will converge to the correct solution and convergence is only guaranteed when the starting point for the iteration is "close" to the final solution. This implies that these methods all need a starting point for the process. This will be discussed in more detail under "Starting Point for Process." Most of these methods incorporate techniques to expand the region of convergence (so called global methods). Non global methods are the ones that have been noted in Hansen (U.S. Pat. Nos. 4,622,644, 4,642,786), Rorden et al. (U.S. Pat. No. 4,710,708), Dumoulin et al. (U.S. Pat. No. 5,377,678) and Blood (U.S. Pat. No. 5,600, 330). It should be noted that increasing the region of convergence is most important when first starting the process. It allows the process to converge from poor starting points. Once started, however, a limited region of convergence is ok since the next starting point is based on the last solution that is usually close to the present solution.

The above mentioned Press et al. reference also discusses the method of simulated annealing, a controlled random search method for least squares problems. Another statistically based search method is disclosed in Aluffi-Pentini, Filippo, Parisi, Valerio, Zirilli, Francesco, "ALGORITHM 667, SIGMA: A Stochastic-Integration Global Minimization Algorithm," ACM Transactions on Mathematical Software, Vol. 14, No. 4, December 1988, pages 366–380.

The following are useful for solving non-linear system of equations, based on successive substitutions instead of simultaneous solutions (as done in Newton methods):

More, Jorge J., Cosnard, Michel Y. "ALGORITHM 554, BRENTM, A Fortran Subroutine for the Numerical Solution of Systems of Nonlinear Equations." ACM Transactions on Mathematical Software, Vol. 6, No. 2, June 1980, pages 240–251.

Brown, Kenneth M. "Computer Oriented Algorithms for Solving Systems of Simultaneous Nonlinear Algebraic Equations," in Numerical Solution of Systems of Nonlinear Algebraic Equations, Academic Press, 1973, pages 281–348. They are derivative free and are related to Gaussian elimination in linear equations.

The following is a method of formulating the solution of the non-linear system of equations into a system of ordinary differential equations:

Aluffi-Pentini, Filippo, Parisi, Valerio, Zirilli, Francesco. "ALGORITHM 617, DAFNE: A Differential-Equations Algorithm for Nonlinear Equations." ACM Transactions on Mathematical Software, Vol. 10, No. 3, September 1984, pages 317–324. Standard differential equations processes are than used to solve the problem.

The following are bisection methods that attempt to find the roots of a system of non-linear equations by bisecting an n dimensional space in a systematic manner:

Vrahatis, Michael N. "Solving Systems of Nonlinear Equations Using the Nonzero Value of the Topological Degree." ACM Transactions on Mathematical Software, Vol. 14, No. 4, December 1988, pages 312–329.

Kearfott, R. Baker, "Interval Arithmetic Techniques in the Computational Solution of Nonlinear Systems of Equations: Introduction, Examples, and Comparisons." Lectures in Applied Mathematics, American Mathematical Society, Vol. 26, 1990.

Homotopy/continuation methods are discussed as follows:

Scarf, H., "The Approximation of Fixed Points of a Continuous Mapping," SIAM Journal Applied Mathematics, Vol. 15, 1967, pages 1328–1343 in reference 13. These methods work by constructing a continuous deformation of one set of non-linear equations into the original system of non-linear equations.

The following covers genetic processes that try to evolve a best solution:

Schwefel, Hans-Paul, "Numerical Optimization of Computer Models." John Wiley & Sons, Ltd., 1981.

All these methods (and others not mentioned) can be used to solve the P&O processes that are to be discussed. The various methods require different processing power depending on the size and complexity of the problem. In general, bisection, homotopy, genetic and statistically based methods take much longer to converge than the Newton based methods and are therefore not feasible at the present time for real time use. Bisection and homotopy methods, however, can usually find the global solution from any starting point. Newton methods can be used for real time computation and global Newton methods extend the range between the starting point of the process and the final solution. The methods based on Gaussian elimination are the fastest of the lot but require a starting point relatively close to the solution. The best strategy for starting the process at an arbitrary point might be to use one of the slower methods at start up and switch over to Newton or Gaussian methods once convergence has been achieved.

A point worth mentioning is that the set of equations for the different tracker configurations is variable and that a particular set might be better based on the placement or configuration of the coils. That is, if there are more equations than unknowns, one can formulate the problem as:

1) Solve a system of non-linear equations (m=n).
2) Solve the non-linear least squares problem (m≧n).

Solving a system of non-linear equations can imply using a subset of the equations. Using the least squares approach might mean using all the equations or a subset of the equations. Those familiar with the problem will obviously be able to put together other sets of equations not mentioned here. Using more than the minimum required number of equations using the least squares approach usually reduces the sensitivity of the P&O solution to the model parameters and increases the range of convergence.

Up to this point all discussion of the exact formulation of the underlying equations has been directed towards the B-field generating elements. However, sensing devices, such as coils, are of finite size. The use of the exact equation formulation for the sensed voltages might be necessary depending on the applications accuracy requirements and the sensor coil size. As has been noted in most of the applicable patents the roles of the B-field generators and the B-field sensing elements can be reversed. A similar approach to correcting for the finite size of the sensing coils can be derived and utilized in the P&O process. For most applications, especially those in catheters, this added complexity to the defining equations is neither required nor desired.

Configurations

All of these configurations can be written in a general mathematical format. The general formulation is (in terms of an orthogonal dot product):

$$\lambda_p[\bar{B}_x, \bar{B}_y, \bar{B}_z]_p \cdot \lambda_q[\cos\alpha \cdot \bar{i}, \cos\beta \cdot \bar{j}, \cos\gamma \cdot \bar{k}]_q = v_{p,q} \quad (10)$$

Or, in terms of the problem formulation, $$\lambda_p[\bar{B}_x, \bar{B}_y, \bar{B}_z]_p \cdot \lambda_q[\cos\alpha \cdot \bar{i}, \cos\beta \cdot \bar{j}, \cos\gamma \cdot \bar{k}]_q - v_{p,q} = 0 \quad (11)$$

where $B_x$, $B_y$ and $B_z$ are the x, y and z components of the $p^{th}$ generating coil's B-field; i, j and k are unit vectors in the direction of the Cartesian coordinate axes; $\cos(\alpha)$, $\cos(\beta)$ and $\cos(\gamma)$ are direction cosines of sensor coil q; $\lambda_q$ is the effective area of sensing coil q; $\lambda_p$ represents the number of turns comprising the $p^{th}$ generating coil and, for time varying currents, a term proportional to the negative time derivative of the B-field; and $v_{p,q}$ is the induced voltage at sensing coil q for the $p^{th}$ generating coil. The unknowns are the x, y and z position of the sensing coil and the 3q direction cosines. For 1 sensing coil q=1.

It is also possible to rewrite the above in terms of the sensing coils azimuth (A) and elevation (E). $\cos(\alpha)$, $\cos(\beta)$ and $\cos(\gamma)$ are then replaced by $\cos(A)\cos(E)$, $\sin(A)\cos(E)$ and $-\sin(E)$, respectively. The unknowns are now one less than before, i.e., x, y and z position of the sensing coil and sensing coil azimuth and elevation (hence 5DOF).

Figure 3:
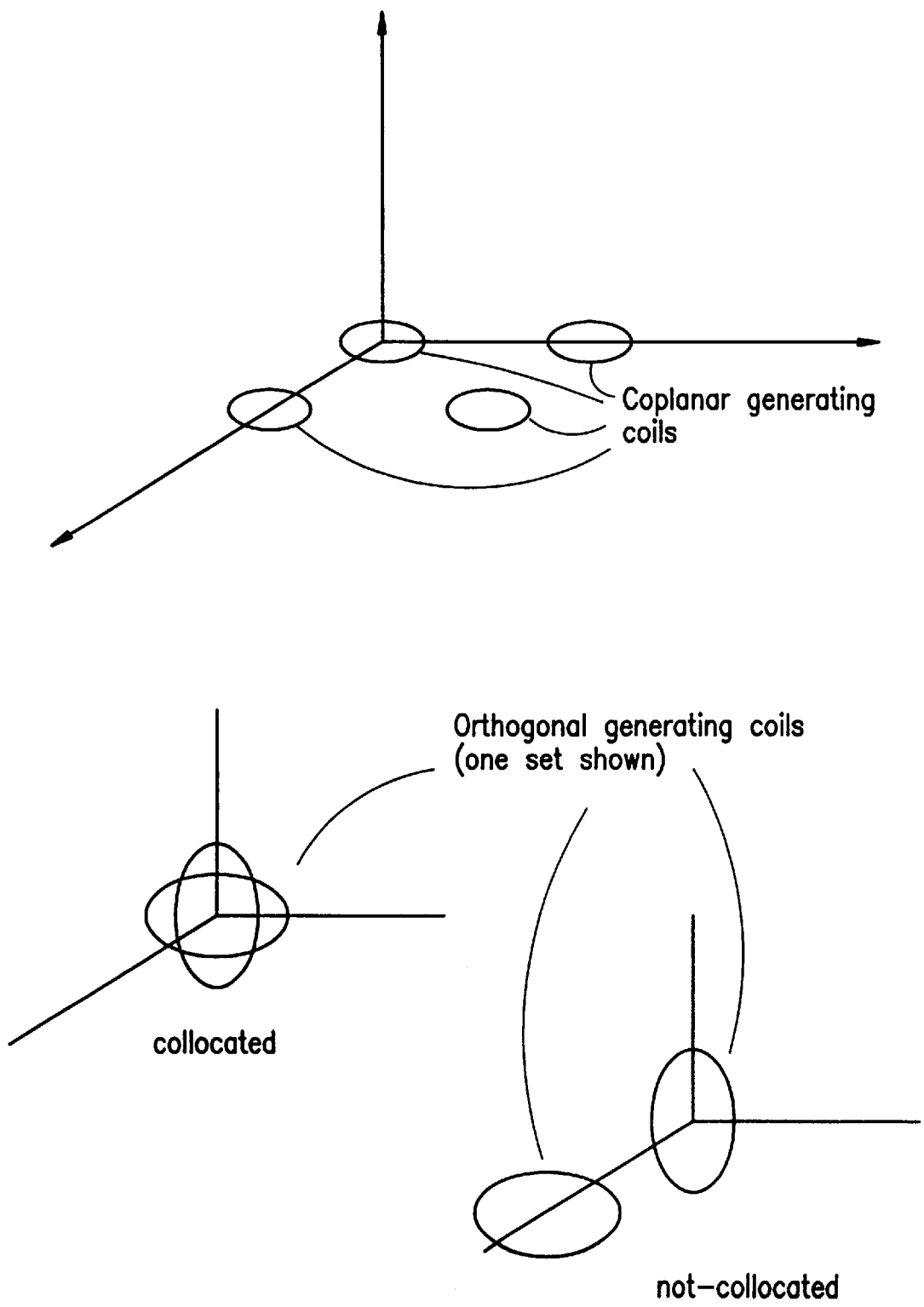

4 Generating Coils, 1 Sensing Coil 4 generating coils (p=4) can be placed at arbitrary positions and orientations as long as they are not collocated and oriented the same way. The coils should be arranged such that symmetries are minimized to prevent places having the same B-fields for different positions and orientations. The 4 generating coils may be coplanar or be two sets of orthogonal coils or anything else (FIG. 3). The 4 B-field equations can be solved as a non-linear systems of equations problem by adding the additional equation that the sum of the squares of the direction cosines must sum to 1, i.e., $$\cos^2\alpha + \cos^2\beta + \cos^2\gamma - 1 = 0 \quad (12)$$

which is equivalent to $$(\cos A \cos E)^2 + (\sin A \cos E)^2 + (-\sin E)^2 - 1 = 0 \quad (13)$$

Now m=5 and n=5.

5 Generating Coils, 1 Sensing Coil 5 generating coils (p=5) can be placed at arbitrary positions and orientations as long as they are not collocated and oriented the same way. The coils should be arranged such that symmetries are minimized to prevent places having the same B-fields for different positions and orientations. The 5 generating coils may be coplanar or be two sets of collocated orthogonal coils with a fifth coil arbitrarily placed or anything else. The 5 B-field equations can be solved as a non-linear systems of equations problem (m=5, n=5) or solved as a least squares problem by adding the additional equation that the sum of the squares of the direction cosines must sum to 1, as above. Now m=6 and n=5.

6 or More Generating Coils, 1 Sensing Coil

6+ generating coils (p=6+) can be placed at arbitrary positions and orientations as long as they are not collocated and oriented the same way. The coils should be arranged such that symmetries are minimized to prevent places having the same B-fields for different positions and orientations. The 6+ generating coils may be coplanar or be two sets of 3-axis orthogonal coils or 3 sets of 2-axis orthogonal coils or anything else. The 6 coil problem can be solved as a non-linear systems of equations using the 6 B-field equations (m=6, n=6) where the unknowns are x, y and z position and the 3 direction cosines. Or it can be solved as a least squares problem by adding the additional equation that the sum of the squares of the direction cosines must sum to 1, as above. Now m=7 and n=6. Adding additional coils adds additional equations (increasing m) for the least squares problem to fit to. While this can reduce the errors in the P&O solution and increase the region of convergence, it does so at the expense of processing time.

Figure 4:
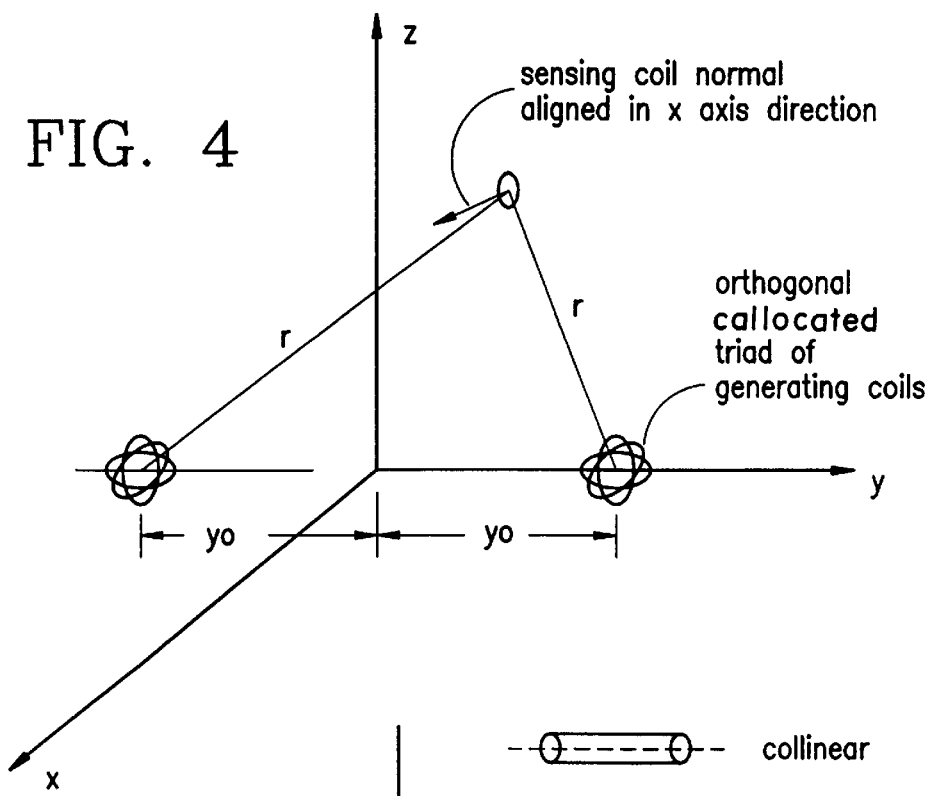

A special configuration of generating coils should be noted. Hansen (U.S. Pat. No. 4,622,644) and Rorden et al. (U.S. Pat. No. 4,710,708) both note that there are ambiguities when 2 sets of 3 collocated orthogonal generating coils are used. This can be best understood by examining a specific configuration where the 2 sets of triads are located symmetrically about the origin on the y-axis at a distance $y_0$ as shown in FIG. 4. The sensing coil is place exactly between the two triads (y=0) and is oriented such that $\cos(\alpha)=1$, $\cos(\beta)=0$ and $\cos(\gamma)=0$. writing the equations one sees that there are only 4 unique equations, i.e., equation (14) and (15) are identical with equation (17) and (18). This results in a matrix that is not of full rank (there are only 4 independent equations from the set of six). The mathematical methods used by Hansen and Rorden et al. could not handle this problem. However the Algorithm 573 article and Tensor Methods for Nonlinear Equations article as previously mentioned, among others, can solve rank deficient systems of non-linear equations and least squares problems without encountering the problems noted by Hansen and Rorden et al.

2 Generating Coils, 2 Sensing Coils 2 generating coils (p=2) can be placed at arbitrary positions and orientations as long as they are not collocated and oriented the same way. The coils should be arranged such that symmetries are minimized to prevent places having the same B-fields for different positions and orientations. The 2 generating coils may be coplanar or collinear or be a set of collocated orthogonal coils or anything else.

Figure 5:
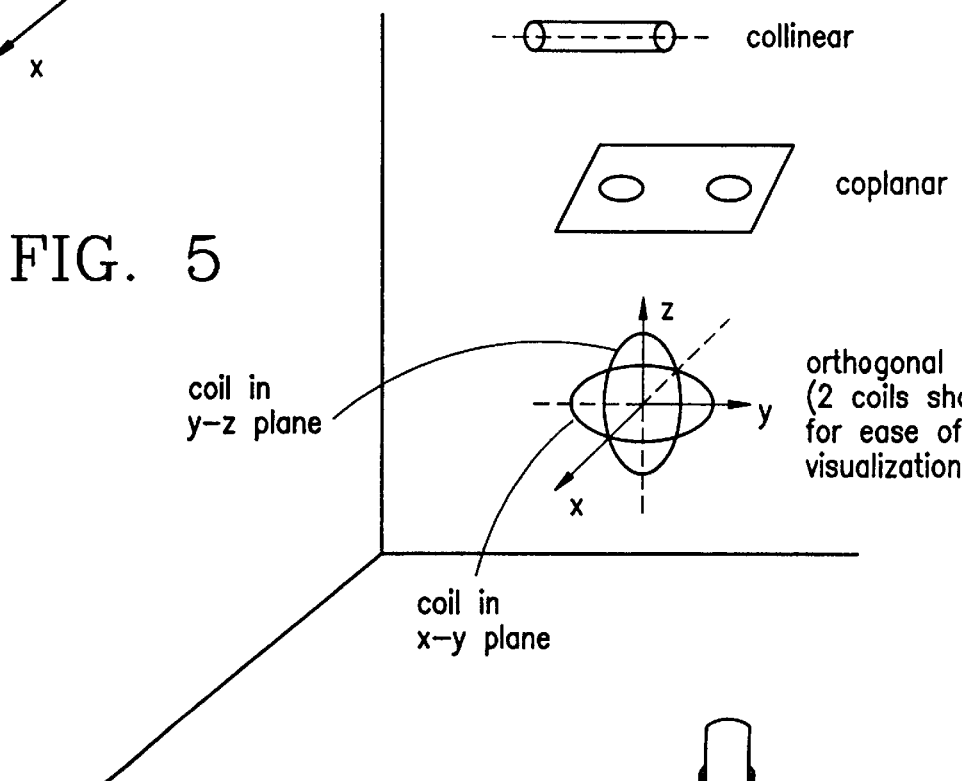

The 2 sensing coils (q=2) can be orthogonal, coplanar or collinear or some other combination as long as they are not collocated and oriented the same way (FIG. 5). There are now 2 B-field equations per 2 sensing coils for a total of 4 equations. A 5DOF system is obtained if the 2 sensing coil normals are collinear. Coplanar coils might seem to yield a 5DOF system since the coils are both oriented the same way. However, 6DOF is possible because the 2 coil centers define a plane without axial symmetry. Rotation about the sensing coil plane's x and z-axis is defined by the relative positions of the 2 coils. This and the coil normal are sufficient to determine the 3DOF required for orientation. For the case where they are not oriented in the same direction, e.g., orthogonal, a 6DOF system is also obtained. Expressed in terms of equation (11), there are 9 unknowns. The unknowns are the x, y and z position of the sensing coils and the 6 direction cosines.

Two or more additional equations are still needed to use the methods mentioned above. Two obvious equations are:

$$\cos^2 \alpha_1 + \cos^2 \beta_1 + \cos^2 \gamma_1 - 1 = 0 \qquad (20)$$

$$\cos^2 \alpha_2 + \cos^2 \beta_2 + \cos^2 \gamma_2 - 1 = 0 \qquad (21)$$

$$v_{1,1} = \lambda_1 \lambda_1 \left( \frac{g\mu_0 I}{2\pi} \frac{xz}{(x^2+(y+y_0)^2)\sqrt{\left(a+\sqrt{x^2+(y+y_0)^2}\right)^2 + z^2}} \left( -K(\alpha) + E(\alpha) \frac{a^2+x^2+(y+y_0)^2+z^2}{\left(a-\sqrt{x^2+(y+y_0)^2}\right)^2 + z^2} \right) \right) \qquad (14)$$

$$v_{2,1} = \lambda_2 \lambda_1 \left( \frac{g\mu_0 I}{2\pi} \frac{1}{\sqrt{\left(a+\sqrt{(y+y_0)^2+z^2}\right)^2 + x^2}} \left( K(\alpha) + E(\alpha) \frac{a^2-x^2-(y+y_0)^2-z^2}{\left(a-\sqrt{(y+y_0)^2+z^2}\right)^2 + x^2} \right) \right) \qquad (15)$$

$$v_{3,1} = \lambda_3 \lambda_1 \left( \frac{g\mu_0 I}{2\pi} \frac{x(y+y_0)}{(x^2+z^2)\sqrt{\left(a+\sqrt{x^2+z^2}\right)^2 + (y+y_0)^2}} \left( -K(\alpha) + E(\alpha) \frac{a^2+x^2+(y+y_0)^2+z^2}{\left(a-\sqrt{x^2+z^2}\right)^2 + (y+y_0)^2} \right) \right) \qquad (16)$$

$$v_{4,1} = \lambda_4 \lambda_1 \left( \frac{g\mu_0 I}{2\pi} \frac{xz}{(x^2+(y-y_0)^2)\sqrt{\left(a+\sqrt{x^2+(y-y_0)^2}\right)^2 + z^2}} \left( -K(\alpha) + E(\alpha) \frac{a^2+x^2+(y-y_0)^2+z^2}{\left(a-\sqrt{x^2+(y-y_0)^2}\right)^2 + z^2} \right) \right) \qquad (17)$$

$$v_{5,1} = \lambda_5 \lambda_1 \left( \frac{g\mu_0 I}{2\pi} \frac{1}{\sqrt{\left(a+\sqrt{(y-y_0)^2+z^2}\right)^2 + x^2}} \left( K(\alpha) + E(\alpha) \frac{a^2-x^2-(y-y_0)^2-z^2}{\left(a-\sqrt{(y-y_0)^2+z^2}\right)^2 + x^2} \right) \right) \qquad (18)$$

$$v_{6,1} = \lambda_6 \lambda_1 \left( \frac{g\mu_0 I}{2\pi} \frac{x(y-y_0)}{(x^2+z^2)\sqrt{\left(a+\sqrt{x^2+z^2}\right)^2 + (y-y_0)^2}} \left( -K(\alpha) + E(\alpha) \frac{a^2+x^2+(y-y_0)^2+z^2}{\left(a-\sqrt{x^2+z^2}\right)^2 + (y-y_0)^2} \right) \right) \qquad (19)$$

Also, as noted earlier in the 4 Generating Coils, 1 Sensing Coil configuration, it is possible to add the sensing coil normal equation to this configuration and obtain 5 equations with the 5 unknowns of X, y, z, azimuth and elevation.

However, this introduces 3 more unknowns. For sensing coils that are not collinear or coplanar one can also write:

$$\cos \alpha_1 \cos \alpha_2 + \cos \beta_1 \cos \beta_2 + \cos \gamma_1 \cos \gamma_2 = k_1 \qquad (22)$$

$$(\cos\beta_1 \cos\gamma_2 - \cos\gamma_1 \cos\beta_2)^2 + (\cos\gamma_1 \cos\alpha_2 - \cos\alpha_1 \cos\gamma_2)^2 +$$
$$(\cos\alpha_1 \cos\beta_2 - \cos\beta_1 \cos\alpha_2)^2 = k_2 \quad (23)$$

Figure 6:
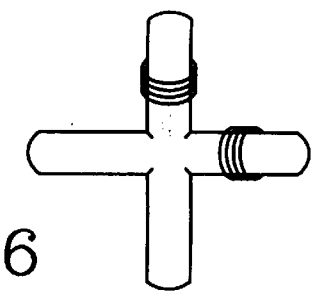
FIG. 6 is a front view of a two coil structure used with some embodiments of the present invention.

Equation (22) is derived from the definition from the vector dot product. Equation (23) is derived from the definition from the vector cross product. $k_1$ represents the cosine of the angle between the two sensor coil normals and $k_2$ represents the sine of the angle between the two sensor coil normals. When the sensor coils are orthogonal $k_1$ is identically 0 and $k_2$ is identically 1. This can be achieved readily by winding the sensor coils on a mandrel as shown in FIG. 6. When sensing coils are either coplanar or collinear $k_1$ is identically 1 and $k_2$ is identically 0. It should be noted again that when the sensing coil normals are collinear the system is only a 5DOF measurement system.

Figure 7A:
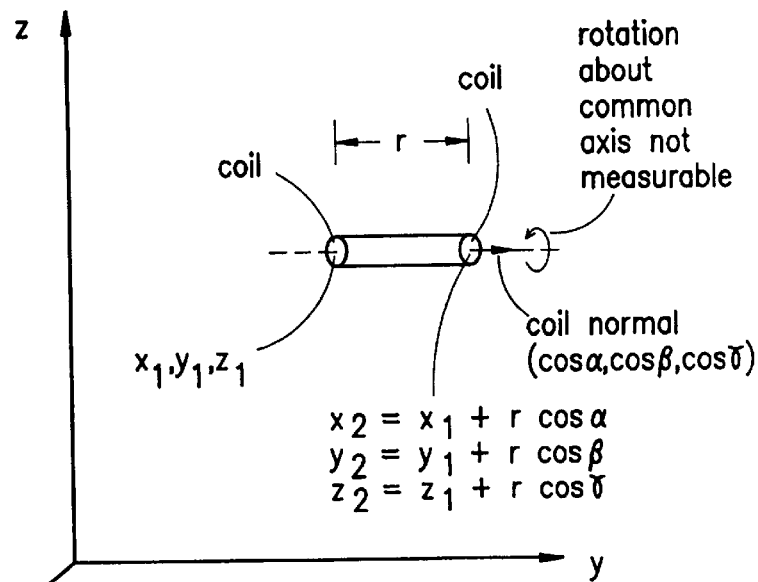
FIGS. 7A, 7B, and 8–10 are simplified xyz schematic diagrams for explaining the derivation of various equations and configurations used with the present invention.
Figure 7B:
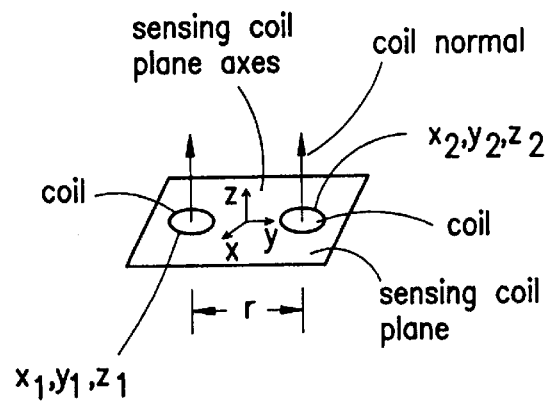

Since the 2 sensing coils are not at the same position (even if they were wound around one another they might not be perfectly collocated), the following substitutions (analogous to those for displacing the generating coils) are required to reference the sensor coils to a common sensing point:

$$x_1 = x - r_1 \cos(\alpha_1) \quad (24)$$

$$y_1 = y - r_1 \cos(\beta_1) \quad (25)$$

$$z_1 = z - r_1 \cos(\gamma_1) \quad (26)$$

and $$x_2 = x - r_2 \cos(\alpha_2) \quad (27)$$

$$y_2 = y - r_2 \cos(\beta_2) \quad (28)$$

$$z_2 = z - r_2 \cos(\gamma_2) \quad (29)$$

where $r_1$ and $r_2$ represent the distance between the center of each sensor coil and the point x, y, z (see FIG. 7).
Now we can write:

$$r_1 = \sqrt{(x-x_1)^1 + (y-y_1)^1 + (z-z_1)^1} \quad (30)$$

$$r_2 = \sqrt{(x-x_2)^2 + (y-y_2)^2 + (z-z_2)^2} \quad (31)$$

There are now ten equations (m=10) to choose from to solve for the 9 unknowns (n=9). Of course, one of the coil centers can be taken as the common reference point. This would eliminate one equation (m=9).

The direction cosines for an orthogonal set of sensor coils can be represented in terms of azimuth, elevation and roll (R). For orthogonally placed sensing coils equation (20) and (21) be rewritten as:

$$(\cos A \cos E)^2 + (\sin A \cos E)^2 + (-\sin E)^2 - 1 = 0 \quad (32)$$

$$(-\cos R \sin A + \sin R \sin E \cos A)^2 + (\cos R \cos A + \sin R \sin E \sin A)^2 + (\sin R \cos E)^2 - 1 = 0 \quad (33)$$

This formulation is now also sufficient to solve the problem. Likewise, equation (22) and (23) can be rewritten in terms of azimuth, elevation and roll. This would provide additional equations for a non-linear least squares solution.

2 Generating Coils, 3 Sensing Coils 2 generating coils (p=2) can be placed at arbitrary positions and orientations as long as they are not collocated and oriented the same way. The coils should be arranged such that symmetries are minimized to prevent places having the same B-fields for different positions and orientations. The 2 generating coils may be coplanar or collinear or be a set of collocated orthogonal coils or anything else. Such different coil configurations are shown in FIG. 5.

The 3 sensing coils (q=3) can be orthogonal, coplanar or collinear or some other combination as long as they are not collocated and oriented the same way. There are now 2 B-field equations per sensing coil for a total of 6 equations. Either 5DOF or 6DOF systems can be constructed depending on whether the sensing coils are collinear, coplanar or whether they are oriented differently. The unknowns are the x, y and z position of the sensing coils and the 9 direction cosines. Expressed in terms of equation (11) there are 12 unknowns.

Six or more additional equations are needed to solve for position and orientation. Three obvious equations are:

$$\cos^2\alpha_1 + \cos^2\beta_1 + \cos^2\gamma_1 - 1 = 0 \quad (34)$$

$$\cos^2\alpha_2 + \cos^2\beta_2 + \cos^2\gamma_2 - 1 = 0 \quad (35)$$

$$\cos^2\alpha_3 + \cos^2\beta_3 + \cos^2\gamma_3 - 1 = 0 \quad (36)$$

However, this introduces 6 more unknowns. For sensing coils that are not collinear or coplanar one can also write:

$$\cos\alpha_1 \cos\alpha_2 + \cos\beta_1 \cos\beta_2 + \cos\gamma_1 \cos\gamma_2 = k_1 \quad (37)$$

$$\cos\alpha_1 \cos\alpha_3 + \cos\beta_1 \cos\beta_3 + \cos\gamma_1 \cos\gamma_3 = k_2 \quad (38)$$

$$\cos\alpha_2 \cos\alpha_3 + \cos\beta_2 \cos\beta_3 + \cos\gamma_2 \cos\gamma_3 = k_3 \quad (39)$$

$$(\cos\beta_1 \cos\gamma_2 - \cos\gamma_1 \cos\beta_2)^2 + (\cos\gamma_1 \cos\alpha_2 - \cos\alpha_1 \cos\gamma_2)^2 +$$
$$(\cos\alpha_1 \cos\beta_2 - \cos\beta_1 \cos\alpha_2)^2 = k_4 \quad (40)$$

$$(\cos\beta_1 \cos\gamma_3 - \cos\gamma_1 \cos\beta_3)^2 + (\cos\gamma_1 \cos\alpha_3 - \cos\alpha_1 \cos\gamma_3)^2 +$$
$$(\cos\alpha_1 \cos\beta_3 - \cos\beta_1 \cos\alpha_3)^2 = k_5 \quad (41)$$

$$(\cos\beta_2 \cos\gamma_3 - \cos\gamma_2 \cos\beta_3)^2 + (\cos\gamma_2 \cos\alpha_3 - \cos\alpha_2 \cos\gamma_3)^2 +$$
$$(\cos\alpha_2 \cos\beta_3 - \cos\beta_2 \cos\alpha_3)^2 = k_6 \quad (42)$$

Equations (37–39) are derived from the definition from the vector dot product. Equations (40–42) are derived from the definition from the vector cross product. $k_1$–$k_3$ represents the cosine of the angle between two sensor coil normals and $k_4$–$k_6$ represents the sine of the angle between two sensor coil normals. When the sensor coils are orthogonal $k_1$–$k_3$ are identically 0 and $k_4$–$k_6$ are identically 1. this can be achieved readily by winding the sensor coils on a mandrel as shown in FIG. 6. When sensing coils are either all coplanar or collinear $k_1$–$k_3$ are identically 1 and $k_4$–$k_6$ are identically 0. It should be noted again that when the sensing coils are all collinear the system is only a 5DOF measurement system. Other combinations such as 2 sensing coils coplanar and orthogonal to the third are also possible.

Since the 3 sensing coils are not at the same position (even if they were wound around one another they might not be perfectly collocated), the following substitutions (analogous to those for displacing the generating coils) are required to reference the sensor coils to a common sensing point:

$$x_1 = x - r_1 \cos(\alpha_1) \quad (43)$$

$$y_1 = y - r_1 \cos(\beta_1) \quad (44)$$

$$z_1 = z - r_1 \cos(\gamma_1) \quad (45)$$

and $$x_2 = x - r_2 \cos(\alpha_2) \quad (46)$$

$$y_2 = y - r_2 \cos(\beta_2) \quad (47)$$

$$z_2 = z - r_2 \cos(\gamma_2) \quad (48)$$

and $$x_3 = x - r_3 \cos(\alpha_3) \quad (49)$$

$$y_3 = y - r_3 \cos(\beta_3) \quad (50)$$

$$z_3 = z - r_3 \cos(\gamma_3) \quad (51)$$

where $r_1$, $r_2$ and $r_3$ represent the distance between the center of each sensor coil and the point x, y, z.

Now we can write:

$$r_1 = \sqrt{(x-x_1)^2 + (y-y_1)^2 + (z-z_1)^2} \quad (52)$$

$$r_1 = \sqrt{(x-x_2)^2 + (y-y_2)^2 + (z-z_2)^2} \quad (53)$$

$$r_1 = \sqrt{(x-x_3)^2 + (y-y_3)^2 + (z-z_3)^2} \quad (54)$$

There are now 18 equations (m=18) to choose from to solve for the 12 unknowns (n=12). Of course, one of the coil centers can be taken as the common reference point. This would eliminate one equation (m=17). The direction cosines for an orthogonal set of sensing coils can be represented by azimuth, elevation and roll. For orthogonally placed sensing coils equations (31–33) can be replaced by $$(\cos A \cos E)^2 + (\sin A \cos E)^2 + (-\sin E)^2 i = 0 \quad (55)$$

$$(-\cos R \sin A + \sin R \sin E \cos A)^2 + (\cos R \cos A + \sin R \sin E \sin A)^2 + (\sin R \cos E)^2 - 1 = 0 \quad (56)$$

$$(\sin R \sin A + \cos R \sin E \cos A)^2 + (-\sin R \cos A + \cos R \sin E \sin A)^2 + (\cos R \cos E)^2 - 1 = 0 \quad (57)$$

This formulation is also sufficient to solve the problem. Likewise, equations (37–42) can be derived in terms of azimuth, elevation and roll. This would provide additional equations for a non-linear least squares solution. Obviously one can keep this process of generating configurations up indefinitely.

Quality of Solution

Ideally, the solution obtained from the chosen P&O process should, when inserted back into the defining equations (i.e., equation 11), yield zero. This is not likely to happen because of:

1) the finite resolution of the numerical representation within the computer,
2) the finite resolution of the measured signals,
3) environmental noise,
4) imprecision of the system constants,
5) distortion of the magnetic fields due to nearby conducting or ferromagnetic materials, etc.

How accurately the P&O solution fits the equations is measured by the norm of the residuals. The norm of the residuals is defined as the square root of the sum of the squares of the values of the equations (11) evaluated at the P&O solution. The norm is what Hansen (U.S. Pat. No. 4,622,644) calls the noise error vector.

Figure 15:
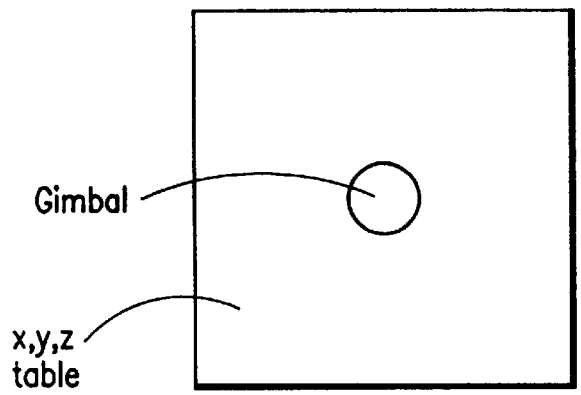
FIG. 15 is a simplified top view of a table and gimbal arrangement used for calibrating the present system.

In practice a characterized system will produce a small but finite norm in an environment that contains no magnetic distorters (highly conductive materials and or ferromagnetic materials) after the P&O process has converged. This value can be determined experimentally during system characterization in a distorter free environment and would, with careful design, cover the first 4 items listed above. Therefore, major increases in the norm can be looked upon as a measure of the decrease in quality of the P&O solution due to distorters within a different environment, e.g., a catheter laboratory. This implies that the norm can be used to qualify whether the P&O solution is accurate enough for a particular application. By noting the range of acceptable norms in a particular environment, a threshold can be set by which the tracking quality can be monitored. When the norm is seen to exceed this threshold due to unexpected environmental noise or the inadvertent introduction of distorting materials a warning can be given such that an inaccurate P&O solution can be noted for evaluation. A flowchart for this process is shown in FIG. 15.

Figure 16:
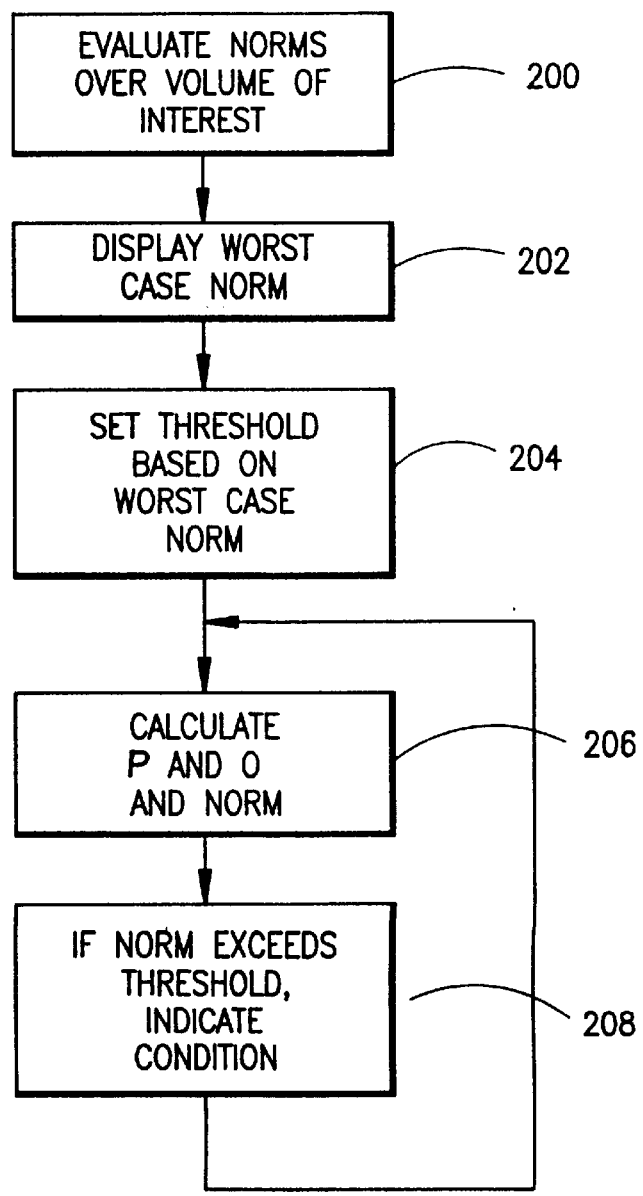
FIGS. 16 and 17 are flowcharts on the use of the norm and residuals comprising the norm as a safety mechanism and a method of compensating for magnetic distortions.

Another use of the norm is in the compensation of magnetic field distortion caused by conductive and ferromagnetic materials. Assume that the norm is sufficiently small in a magnetically clean (no distorters) environment. Now the system is started at either a known P&O in the vicinity of distorters or in a region that is free of distorters. If started at a known P&O, then the residuals making up the norm are a measure of the distortion. These values can be filtered to eliminate noise impulses and subtracted from the next cycles P&O determination. If starting in a region without distortion the residuals are already small. As distorters are now introduced the magnitude of the residuals will increase. The residuals can again be filtered to eliminate noise impulses and subtracted from the next cycles P&O determination. A flowchart of this process is shown in FIG. 16.

Starting Point

A number of ways of providing an initial starting point are possible. One method is to perform a global search of the n dimensional space subject to the physical constraints of the application. This can be a very structured search of the n dimensional space, made by subdividing the space into an n dimensional grid and visiting every point on the grid. The subset of grid points with an acceptably small norm would then be tested in the P&O process until the global solution that best minimizes the norm is found. Another method is to perform an n dimensional random search of the space. The random points are tested in the P&O process until the best solution (minimal norm) is found. There are also systematic methods as described by Aird, T. and Rice, J. in "Systematic Search in High Dimensional Sets," SIAM Journal Numerical Analysis, Vol. 14, No. 2, April 1977. Again, the points are tested in the P&O process until the best solution (minimal norm) is found. All of these methods suffer from the large quantity of points that need to be evaluated and are therefore expensive in terms of time. Hansen (U.S. Pat. No. 4,622, 644) mentions this approach.

Another starting method is to use global methods such as bisection or homotopy methods. While these methods are expensive in terms of time they can usually find the correct P&O solution.

Figure 17:
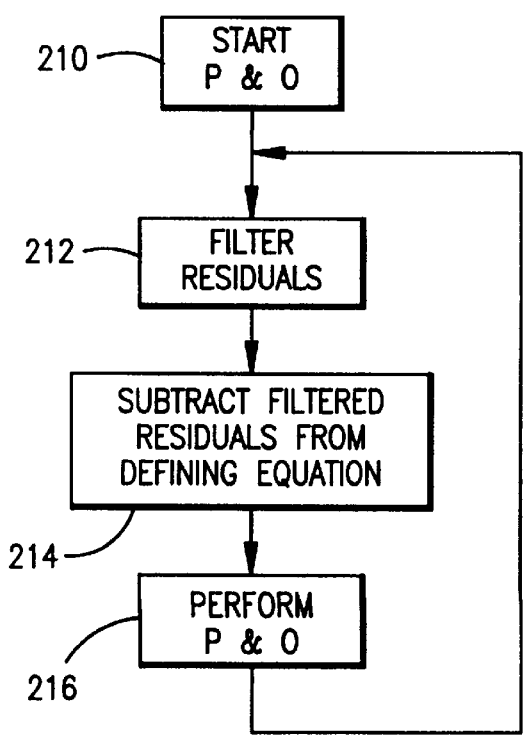

Another way is to place the sensing coil(s) at a known P&O, which is noted in Dumoulin et al. (U.S. Pat. No. 5,377,678). The process is then started with this P&O as it's initial guess. This guarantees almost immediate convergence. This method can be extended to cover a final gain calibration, e.g., to correct for variations in the effective area ($\lambda_q$) of the catheter sensor. Since the P&O of the sensor is known by virtue of its placement, and, assuming all other characterizations are known, the remaining error in the norm can be assigned to $\lambda_q$. This amounts to adjusting $\lambda_q$ to minimize the norm at the known placement and then using that value until a new catheter sensor is used. A flowchart of this process is shown in FIG. 17.

Once the process has converged correctly, that P&O solution becomes the starting point for the next P&O measurement cycle. As long as drastic changes in actual P&O don't occur between sensing coil measurements this is a valid and simple method for obtaining the processes next starting point. This also implies that the fastest processes for determining P&O and the fastest sensed signal collection should be used to minimize the time between successive P&O computations. This minimizes the sampling time and therefore the amount of movement the sensing coil(s) experiences. That way the starting point is very close to the correct P&O solution.

Starting Point for 1 Sensing Coil

As mentioned above, there are a number of ways of determining an initial starting point for the process. Under certain geometries and configurations the use of the infinitesimal dipole model can yield an approximate starting point. The use of the infinitesimal dipole model for determining a starting point does not invalidate the results disclosed in this patent. It is just another tool for determining a starting point. The following discussions are for circular coils. Other numerical approximations could be determined by those skilled in the art for other geometries and configurations. Specifically, a method for determining a starting point when using a single sensing coil can be realized if the generating coils are arranged as 2 (or more) sets of approximately collocated orthogonal triaxial coils or 3 (or more) sets of collocated orthogonal biaxial coils. This can be derived by utilizing the approximate B-field equations for coils in the y-z, x-z and x-y plane, respectively.

$$\vec{B}_{x-coil} = \frac{\lambda\mu_0 I \pi a^2}{4\pi r^5} \cdot \left((2x^2 - y^2 - z^2)\vec{a}_x + 3xy\vec{a}_y + 3xz\vec{a}_z\right) \quad (58)$$

$$\vec{B}_{y-coil} = \frac{\lambda\mu_0 I \pi a^2}{4\pi r^5} \left(3xy\vec{a}_x + (2y^2 - x^2 - z^2)\vec{a}_y + 3yz\vec{a}_z\right) \quad (59)$$

$$\vec{B}_{z-coil} = \frac{\lambda\mu_0 I \pi a^2}{4\pi r^5} \left(3xz\vec{a}_x + 3yz\vec{a}_y + (2z^2 - x^2 - y^2)\vec{a}_z\right) \quad (60)$$

where $\mu_0$ is the permeability of free space; a is the coil radius; I is the current flowing through the coil; $a_x$, $a_y$ and $a_z$ represent the unit vectors in Cartesian coordinates; r is the distance between the generating and sensing coil; and $\lambda$ represents the number of turns comprising the coil.

Starting Point with 2 Triaxial Generating Coil Sets

Assume $\lambda_p$, $\lambda_q$, $I_p$ and $a_p$ are the same for all coils within a triaxial set and that the sets are collocated and orthogonal. Now assume that the sensing coil is oriented such that $\cos(\alpha)=1$, $\cos(\beta)=0$ and $\cos(\gamma)=0$. Based on equation (11) the induced voltages for the triaxial coil set at the origin are:

$$v_{1,1} = \frac{\lambda_p \lambda_q \mu_0 I_p \pi a_p^2}{4\pi r^5}(2x^2 - y^2 - z^2) \quad (61)$$

$$v_{2,1} = \frac{\lambda_p \lambda_q \mu_0 I_p \pi a_p^2}{4\pi r^5}(3xy) \quad (62)$$

$$v_{3,1} = \frac{\lambda_p \lambda_q \mu_0 I_p \pi a_p^2}{4\pi r^5}(3xz) \quad (63)$$

Squaring and summing and taking the square root of the equations one gets:

$$\sqrt{v_{1,1}^2 + v_{2,1}^2 + v_{3,1}^2} = \quad (64)$$

-continued
$$\frac{\lambda_p \lambda_q \mu_0 I_p \pi a_p^2}{4\pi r^5}\sqrt{(2x^2 - y^2 - z^2)^2 + (3xy)^2 + (3xz)^2} =$$

$$\frac{\lambda_p \lambda_q \mu_0 I_p \pi a_p^2}{4\pi r^5}\sqrt{(4x^2 + y^2 + z^2)(x^2 + y^2 + z^2)} =$$

$$\frac{\lambda_p \lambda_q \mu_0 I_p \pi a_p^2}{4\pi r^5}\sqrt{(r^2 + 3x^2)r^2}$$

Using the binomial expansion on the $r^2+3x^2$ term (assuming $r^2 > 3x^2$) and simplifying equation (64) you obtain $$\sqrt{v_{1,1}^2 + v_{2,1}^2 + v_{3,1}^2} = \frac{\lambda_p \lambda_q \mu_0 I_p \pi a_p^2}{4\pi r^3} \quad (65)$$

Figure 8:
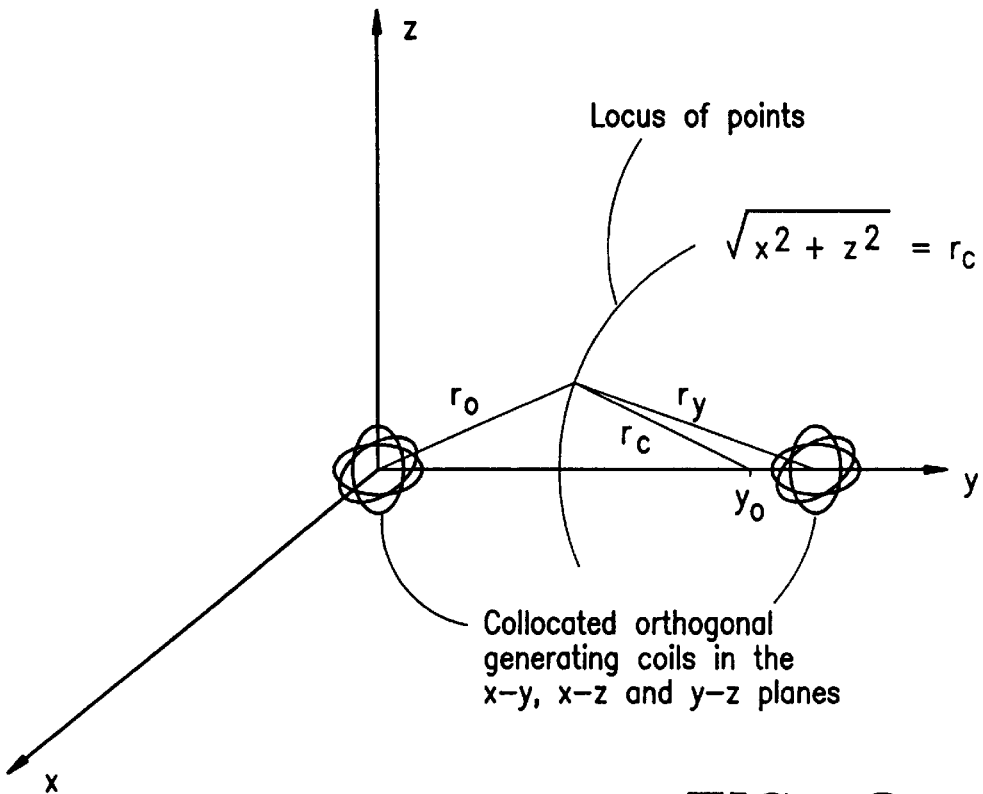

This can be solved for r (now referred to as $r_0$). Likewise, a $r_y$ can be determined for the other triad of generating coils. Referring to FIG. 8 one can see that knowing the r from both sets of triads defines a circle in the x-z plane with radius $r_c$ and centered at (0, $y_0$, 0). This locus of points defines a fixed y coordinate and x and z coordinate pairs that lie on the circle $$r_c^2 = x^2 + z^2 \quad (66)$$

Points on the circle can now be tested in the P&O process.

Starting Point with 3 Biaxial Generating Coil Sets

Figure 9:
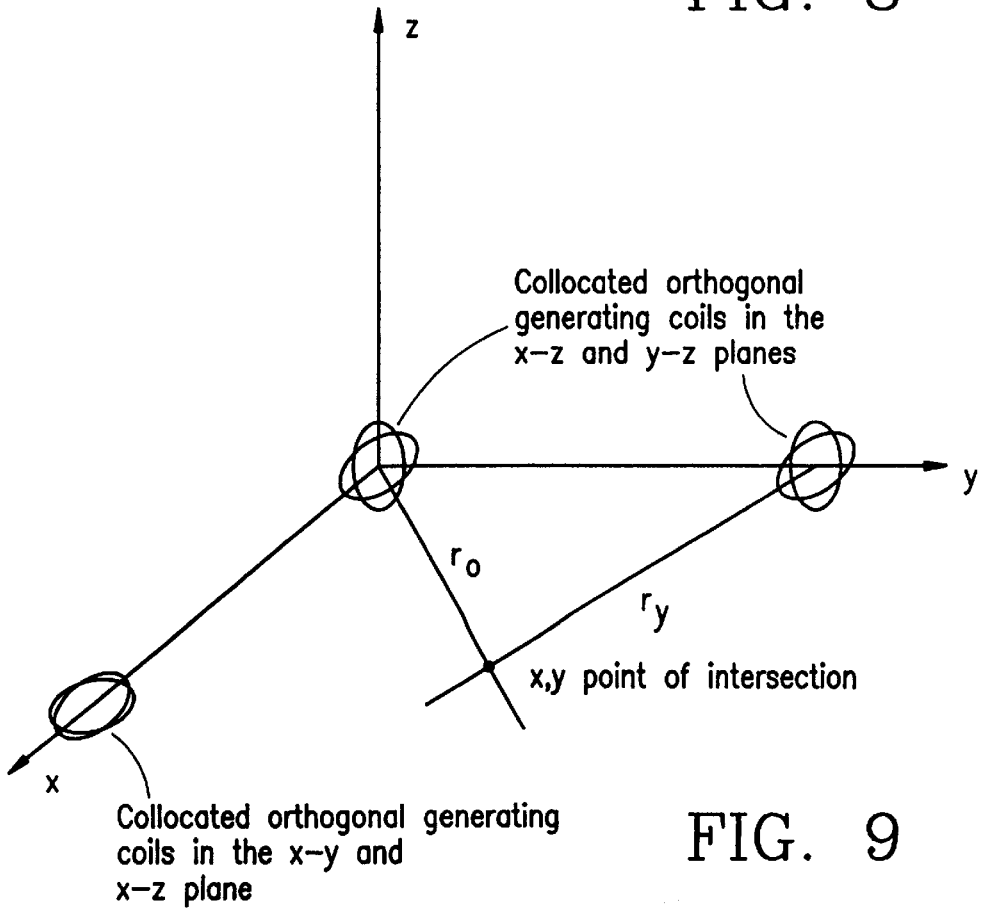

Assume $\lambda_p$, $\lambda_q$, $I_p$ and $a_p$ are the same for all coils within a biaxial generating set and that they are collocated and orthogonal. Place coils in the y-z and x-z planes at the origin. Place this same configuration on the y-axis. Place a biaxial set on the x-axis, but this time place the coils in the x-y and x-z plane (see FIG. 9). Now assume that the sensing coil is oriented such that $\cos(\alpha)=0$, $\cos(\beta)=0$ and $\cos(\gamma)=1$. Based on equation (11) the induced voltages due to the set at the origin are:

$$v_{1,1} = \frac{\lambda_p \lambda_q \mu_0 I_p \pi a_p^2}{4\pi r^5}(3xz) \quad (67)$$

$$v_{2,1} = \frac{\lambda_p \lambda_q \mu_0 I_p \pi a_p^2}{4\pi r^5}(3yz) \quad (68)$$

The ratio of these two equations defines a line in the x-y plane $$\frac{v_{2,1}}{v_{1,1}} = \frac{y}{x} \quad (69)$$

Likewise, another line in the x-y plane can be derived for the biaxial set located on the y-axis. The intersection of these two lines yields a solution point x,y. This can be substituted into $$\frac{v_{6,1}}{v_{5,1}} = \frac{\frac{\lambda_p \lambda_q \mu_0 I_p \pi a_p^2}{4\pi r^5}(2z^2 - x^2 - y^2)}{\frac{\lambda_p \lambda_q \mu_0 I_p \pi a_p^2}{4\pi r^5}(3yz)} \quad (70)$$

which is the ratio of the voltages for the coils on the x-axis. The x and y values are substituted into this equation to solve for z.

Starting Point for 2 Sensing Coils

The general comments from the previous section apply here also. A specific example for the 2 generating coils and 2 sensing coils starting point will be derived in a similar manner to that discussed in Starting Point with 2 Triaxial Generating Coils, above.

Starting Point with 1 Biaxial Generating Coil Set

Figure 10:
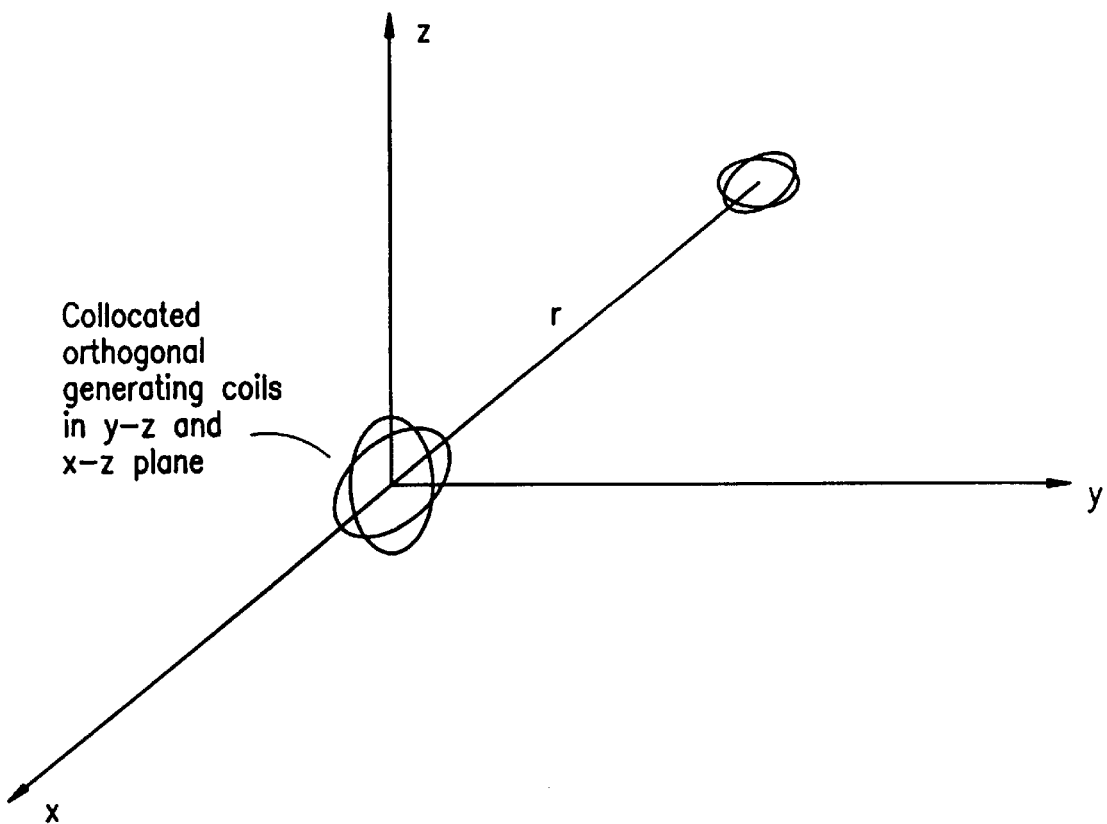

Assume $\lambda_p$, $\lambda_q$, $I_p$ and $a_p$ are the same for all coils within the biaxial generating set and that it is collocated and orthogonal. Place the coils in the y-z and x-z planes at the origin. Now assume that one sensing coil is oriented such that $\cos(\alpha)=0$, $\cos(\beta)=0$ and $\cos(\gamma)=1$ and the other sensing coil is oriented such that $\cos(\alpha)=0$, $\cos(\beta)=0$ and $\cos(\gamma)=0$ (see FIG. 10). Based on equation (11) the induced voltages at the first sensing coil due to the generating coils at the origin are:

$$v_{1,1} = \frac{\lambda_p \lambda_q \mu_0 I_p \pi a_p^2}{4\pi r^5}(3xz) \tag{71}$$

$$v_{2,1} = \frac{\lambda_p \lambda_q \mu_0 I_p \pi a_p^2}{4\pi r^5}(3yz) \tag{72}$$

The ratio of these two equations defines a line in the x-y plane.

$$\frac{v_{2,1}}{v_{1,1}} = \frac{y}{x} \tag{73}$$

Likewise, the induced voltages at the second sensing coil due to the generating coils are:

$$\frac{v_{2,2}}{v_{2,1}} = \frac{\frac{\lambda_p \lambda_q \mu_0 I_p \pi a_p^2}{4\pi r^5}(2z^2 - x^2 - y^2)}{\frac{\lambda_p \lambda_q \mu_0 I_p \pi a_p^2}{4\pi r^5}(3yz)} \tag{74}$$

Substituting equation (73) into (74) yields a curve, the points of which can now be tested in the P&O process.

Starting Point with 1 Triaxial Generating Coil Set

Assume $\lambda_p$, $\lambda_q$, $I_p$ and $a_p$ are the same for all coils within the triaxial generating set and that it is collocated and orthogonal. Place the coils in the x-y, y-z and x-z planes at the origin. Now assume that one sensing coil is oriented such the $\cos(\alpha)=1$, $\cos(\beta)$ and $\cos(\gamma)=0$ and the other sensing coil is oriented such that $\cos(\alpha)=0$, $\cos(\beta)=1$ and $\cos(\gamma)=0$. Based on equation (11) the induced voltages at the first sensing coil due to the generating coils at the origin are:

$$v_{1,1} = \frac{\lambda_p \lambda_q \mu_0 I_p \pi a_p^2}{4\pi r^5}(2x^2 - y^2 - z^2) \tag{75}$$

$$v_{2,1} = \frac{\lambda_p \lambda_q \mu_0 I_p \pi r_p^2}{4\pi r^5}(3xy) \tag{76}$$

$$v_{3,1} = \frac{\lambda_p \lambda_q \mu_0 I_p \pi a_p^2}{4\pi r^5}(3xz) \tag{77}$$

Voltages at the second sensing coil due to the generating coils at the origin are:

$$v_{1,2} = \frac{\lambda_p \lambda_q \mu_0 I_p \pi a_p^2}{4\pi r^5}(3xy) \tag{78}$$

-continued $$v_{2,2} = \frac{\lambda_p \lambda_q \mu_0 I_p \pi a_p^2}{4\pi r^5}(2y^2 - x^2 - z^2) \tag{79}$$

$$v_{3,2} = \frac{\lambda_p \lambda_q \mu_0 I_p \pi a_p^2}{4\pi r^5}(3yz) \tag{80}$$

Squaring and summing and taking the square root of the equations one gets:

$$\sqrt{v_{1,1}^2 + v_{2,1}^2 + v_{3,1}^2 + v_{1,2}^2 + v_{2,2}^2 + v_{3,2}^2} = \tag{81}$$

$$\frac{\lambda_p \lambda_q \mu_0 I_p \pi a_p^2}{4\pi r^5} \sqrt{(2r^2 + 3x^2 + 3y^2)r^2}$$

Using the binomial expansion and simplifying equation (81) you obtain $$\sqrt{v_{1,1}^2 + v_{2,1}^2 + v_{3,1}^2 + v_{1,2}^2 + v_{2,2}^2 + v_{3,2}^2} = \frac{\lambda_p \lambda_q \mu_0 I_p \pi a_p^2 \sqrt{2}}{4\pi r^3} \tag{82}$$

This can be solved for r. Equation (82) and ratios of $v_{2,1}/v_{3,1}$ and $v_{1,2}/v_{3,2}$ can now be solved for x, y and z.

Similar equations can be derived for other multiple sensor coil starting points.

Preferred Embodiments

The equations given above provide numerous different ways to set up a P&O system. It will be considered in the preferred embodiments that transducers (e.g., coils) used for generating information (e.g., electromagnetic fields) are external to the patient and the transducers used for sensing are in the catheter. However, one could easily reverse that so that generating transducers are in the catheter and sensing transducers are external to the patient and in the locator. Note that the catheter could be more broadly considered a remote device for which one wants to determine location parameters. As used herein, location parameters shall include position and orientation information relative to the catheter (or other remote device).

The discussion will use a first example with eight coils used for field generation and one coil used for sensing. A second example with three generating coils and two sensing coils will then be discussed. These are the preferred embodiments when high accuracy and large regions of convergence are required. A third example will use four coils for field generation and one coil for sensing. A fourth example will use two coils for field generation and two coils for sensing. These last two examples are the preferred embodiments when low accuracy and limited regions of convergence are required. As mentioned previously, an important feature of the invention is the ability to provide 5 or 6 degrees of freedom location parameters when p*q=4. However, extra transducers may also be used to enhance the accuracy of the solution and the region of convergence.

5DOF System

Figure 11:
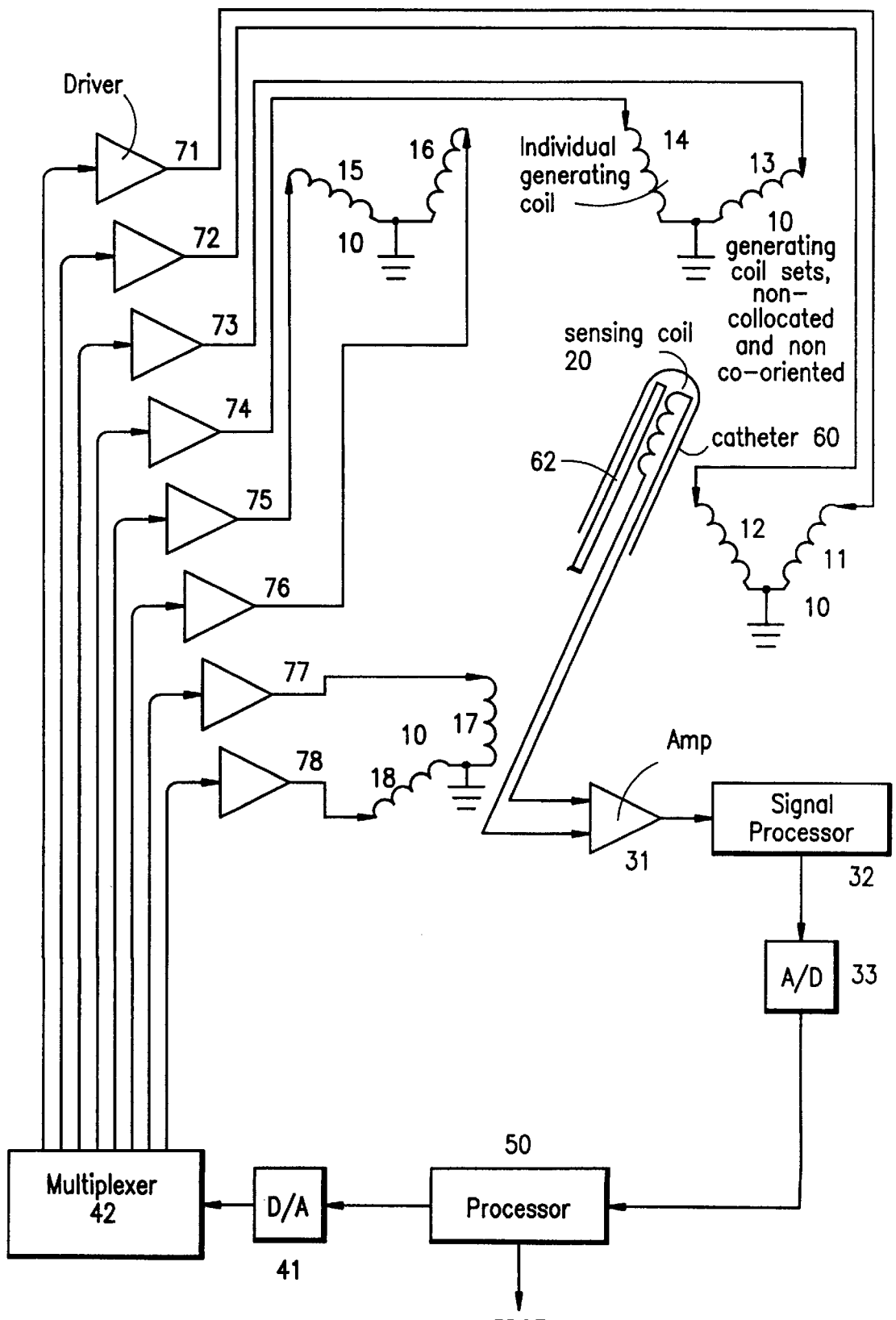
FIGS. 11 and 12 are schematics of two different embodiment systems according to the present invention with 5 degrees of freedom (DOF) measurement capability.

The functional diagram shown in FIG. 11 illustrates the preferred high accuracy 5DOF embodiment. A source of electromagnetic fields is generally illustrated at 10. The source of electromagnetic fields includes a plurality of field-generation means such as generator antennas or coils 11 through 18. While it is known that the minimum configuration requires only 4 B-field generators, it has been found that 8 B-field generators provide a greater region of convergence and a more accurate P&O solution. B-field generators placed as shown can utilize the fastest process by eliminating the possibility of rank deficiency in the P&O process. It is not necessary that there be precisely two B-field generators in a set or that there be eight B-field generators. In the present embodiment, the system operates in the near field. Amplifier 31 18 establish quasi-stationary magnetic fields. Quasi-stationary magnetic fields are low frequency fields that vary so slowly with time that radiation effects are negligible. Although the present embodiment operates in the near field with coils, it should be appreciated that other embodiments may operate in the far field with other transmitting means, and rotating magnets can be substituted for the B-field generator coils.

A signal generator is provided for applying electrical signals to B-field generator coils 11 through 18 to generate a plurality of low frequency electromagnetic field. Any frequency from zero to several hundred kHz may be used. The signals are multiplexed so that: the fields generated by each of the coils are distinguishable. The signal generator is comprised of a digital to analog (D/A) converter 41, a multiplexer 42 and driving amplifiers 71–78 for supplying power to each of the B-field generator coils 11 through 18. The D/A 41 is fed a digitized waveform, typically sinusoidal, from the processor 50, which performs the P&O calculation process. It will be appreciated that the digitized waveform can be adjusted in gain by processor 50 to affect controlled amplitude variations in the generated B-field. This would typically be used to compensate for large variations in sensed signal due to a large range of motion of the sensor, thus forming part of an automatic gain control (AGC) stage controlled by processor 50. The multiplexer comprises a conventional circuit for time division multiplexing the signals applied to each of the B-field generating coils. However, it will be appreciated by those skilled in the art that any one of a number of suitable multiplexing techniques may be employed, including time division multiplexing, frequency division multiplexing, or phase multiplexing and a suitable driver for implementing such a multiplexing technique will be provided.

A sensor 20 receives the electromagnetic fields generated by the source 10. The sensor is a coil but other technologies such as flux gate, Hall effect, and magnetoresistive devices may be used. The sensing device must produce an output proportional to the magnitude of the magnetic field and the cosine of the included angle between the directions of the magnetic field and the sensing device axis. For a coil the direction of the coil is perpendicular to the plane of the coil with the well-known right-hand-rule determining the sense. The output of the sensor coil is input into an amplifier 31. Signal processor 32 then processes the amplified signal. The purpose of the signal processor 32 is to reduce out of band signals from reaching the process processing stage (where P&O is calculated) and affecting the accuracy of the P&O solution. In the preferred embodiment it is a simple low pass filter comprised of a resistor and a capacitor. It should be appreciated that any form of signal processing including none, passive, active analog and switched capacitor could be used depending on the application. In addition, signal processor 32 could contain adjustable gain stages to affect controlled amplification of the sensed sensor signal. This would form part of an AGC stage controlled by processor 50. An analog to digital conversion is then provided at 33.

It should also be appreciated that any number of sensors 20 could be tracked using generating coils 10, drivers 43 through 48, multiplexer 42, D/A 41 and processor 50.

Additional sensors could be multiplexed into amp 31 and then be processed by signal processor 32, A/D 33 and processor 50. Alternately, multiple input channels consisting of sensor 20, amplifier 31, signal processor 32, A/D 33 could be multiplexed into processor 50. Those skilled in the art will obviously note other architectures.

The signal from A/D 33 is then input into a suitable processor 50. The processor may be one or more actual processors optimized for running various parts of the system. A coherent detection is then performed within the processor between the digitized signal and a suitably phase shifted version of the digitized waveforms that drove D/A 41. It should be appreciated that other signal extraction methods could be performed in place of or in addition to coherent detection, including FFTs, auto and cross-correlation, FIR and IIR filtering, etc. These signal processing methods can also be implemented outside the processor and within signal processor 32. Processor 50 now determines the P&0 of sensor 20. Processor 50 controls signal generation and detection, multiplexing and I/O with other systems.

As shown, the sensing coil 20 is disposed in the distal end of a catheter 60 having an optical fiber 62 extending lengthwise therein. The axial direction of the cylindrical sensing coil 20 is preferably collinear with (or at least parallel to) the axis of the catheter 60. The portion of the catheter 60 housing the coil 20 is sufficiently rigid that coil 20 maintains its cylindrical configuration. Except for the details of the location determination arrangement described herein, the catheter may be otherwise constructed as described in the pending U.S. patent application Ser. No. 08/603,483 filed Feb. 20, 1996 in the name of Abela and Bowden. That application, issued as U.S. Pat. No. 5,769,843 on Jun. 23, 1998 is assigned to the assignee of the present application and is hereby incorporated by reference.

Figure 12:
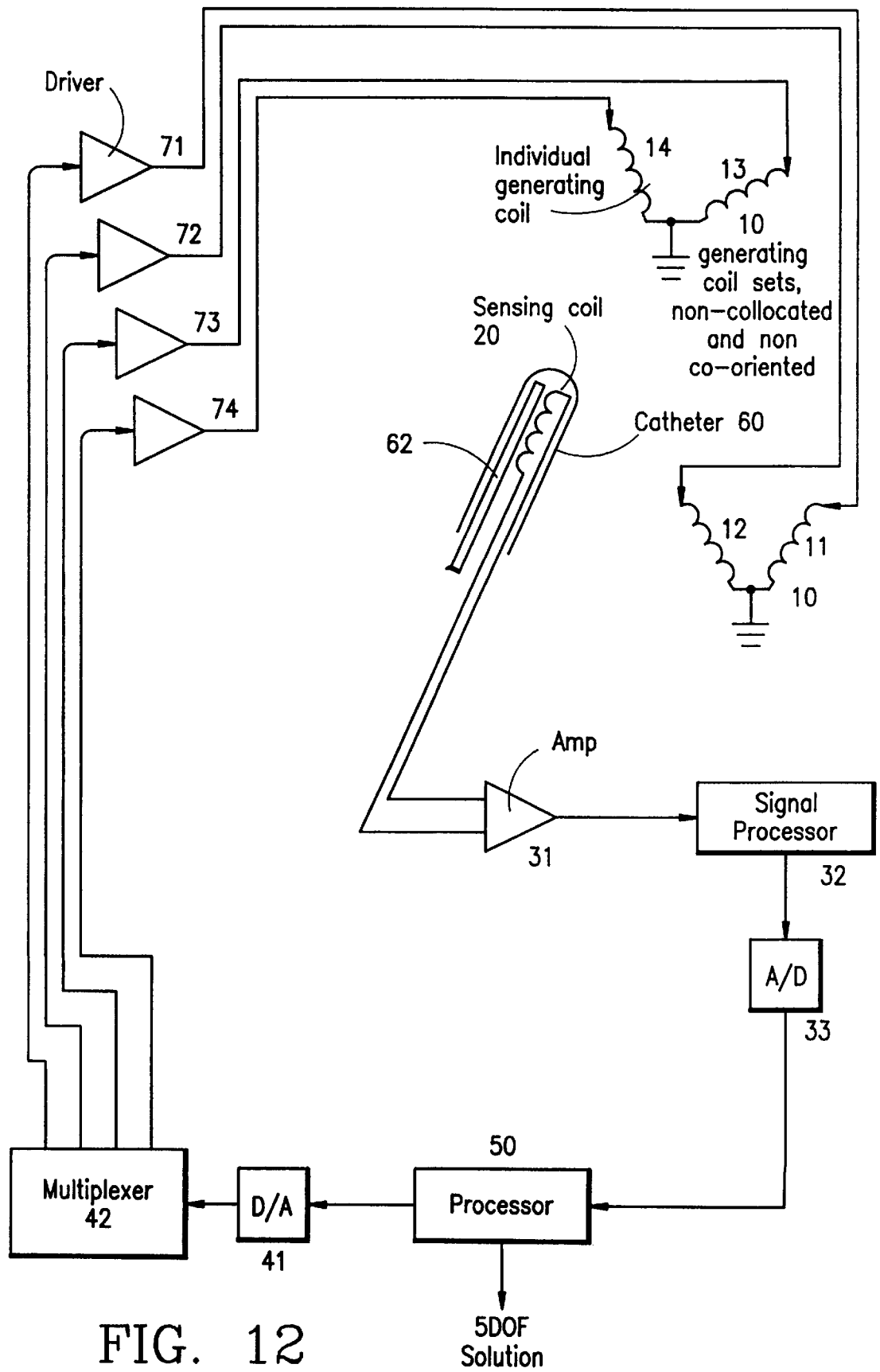

The functional diagram shown in FIG. 12 illustrates the preferred 5DOF embodiment when lower accuracy is acceptable. It is similar to the preferred embodiment illustrated in FIG. 11 with the exception that only 4 generating coils 11, 12, 13, and 14 and four drivers 71, 72, 73, and 74 are required. Therefore, a detailed description of its operation and construction is not required.

Figure 13:
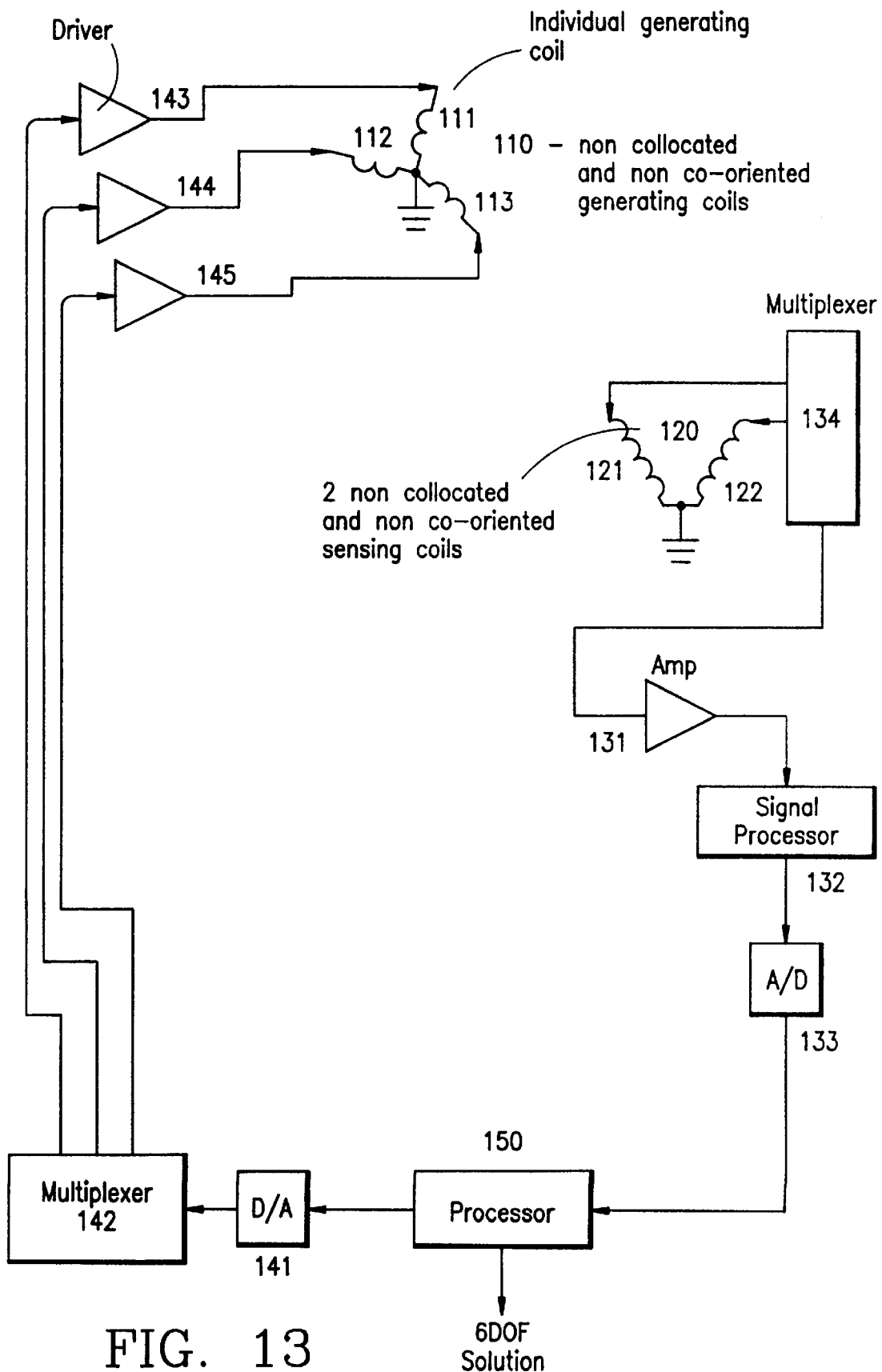
FIGS. 13 and 14 are schematics of two different embodiment systems according to the present invention with 6DOF measurement capability.
Figure 14:
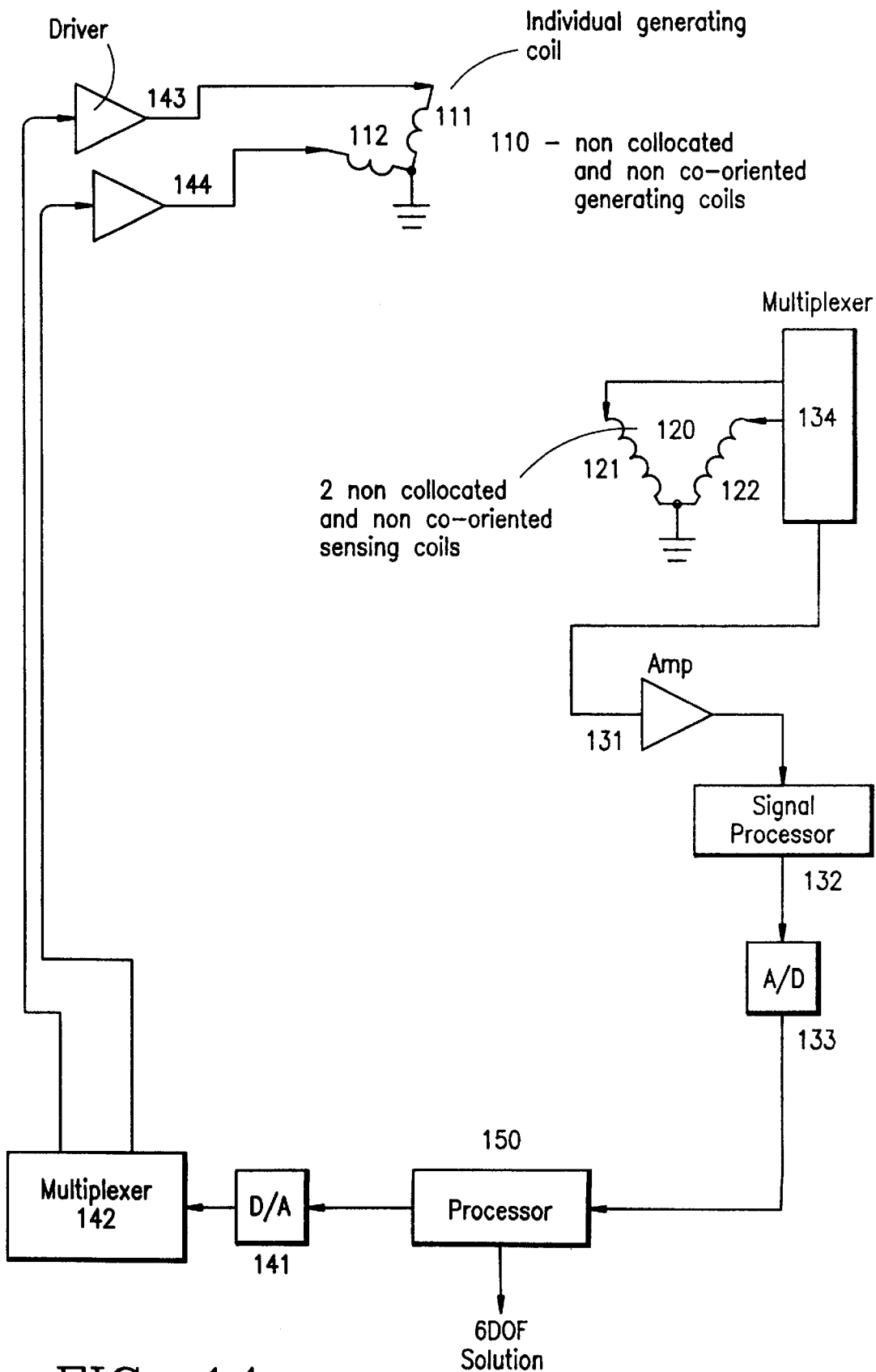

In the discussion that follows, sensing coils of FIGS. 13 and 14 may also be located in a catheter, although the catheter is not shown for ease of illustration.

6DOF System

The functional diagram shown in FIG. 13 illustrates the preferred high accuracy 6DOF embodiment. The components of this embodiment have the same last two digits as the corresponding component of the FIG. 11 embodiment. A source of electromagnetic fields is generally illustrated at 110. The source of electromagnetic fields includes a plurality of field-generation means such as generator antennas 111, 112 and 113. It is not necessary that there be precisely three B-field generators in a set or that there be one B-field generator set. In the present embodiment, the system operates in the near field. Antennas 111 through 113 establish quasi-stationary magnetic fields. Quasi-stationary magnetic fields are low frequency fields that vary so slowly with time that radiation effects are negligible. Although the present embodiment operates in the near field with coils, it should be appreciated that other embodiments may operate in the far field with other transmitting means, and rotating magnets can be substituted for the B-field generators.

A signal generator is provided for applying electrical signals to B-field generator coils 11 through 113 to generate a plurality of low frequency electromagnetic field. Any frequency from zero to several hundred kHz may be used. The signals are multiplexed so that the fields generated by each of the coils are distinguishable. The signal generator is comprised of a digital to analog (D/A) converter 141, a multiplexer 142 and driving amplifiers 143–145 for supplying power to each of the B-field generating coils 111 through 113. The D/A 141 is fed a digitized waveform, typically sinusoidal, from the processor 150. It will be appreciated that the digitized waveform can be adjusted in gain by processor 50 to affect controlled amplitude variations in the generated B-field. This would typically be used to compensate for large variations in sensed signal due to a large range of motion of the sensor, thus forming part of an AGC stage controlled by processor 50. The multiplexer comprises a conventional circuit for time division multiplexing the signals applied to each of the B-field generating coils. However, it will be appreciated by those skilled in the art that any one of a number of suitable multiplexing techniques may be employed, including time division multiplexing, frequency division multiplexing, or phase multiplexing and a suitable driver for implementing such a multiplexing technique will be provided.

A sensor 120 receives the electromagnetic field s generated by the source 110. The sensor is comprised of coils but other technologies such as flux gate, Hall effect, and magneto-resistive devices may be used. The components comprising the sensor must produce an output proportional to the magnitude of the magnetic field and the cosine of the included angle between the directions of the magnetic field and the component axis. The coil outputs are input into multiplexer 134 where each coil can be sampled in a time-multiplexed fashion. The selected coil signal is input into an amplifier 131. Signal processor 132 then processes the amplified signal. The purpose of the signal processor 132 is to reduce out of band signals from reaching the processing stage (where P&O is calculated) and affecting the accuracy of the P&O solution. In the preferred embodiment it is a simple low pass filter comprised of a resistor and a capacitor. It should be appreciated that any form of signal processing including none, passive, active analog and switched capacitor could be used depending on the application. In addition, signal processor 32 could contain adjustable gain stages to affect controlled amplification of the sensed sensor signal. This would form part of an AGC stage controlled by processor 50. An analog to digital conversion is then provided at 133.

It should also be appreciated that any number of sensors 120 could be tracked using generating coils 110, drivers 143–145, multiplexer 142, D/A 141 and processor 150. Additional sensors could multiplexed into amp 131 via multiplexer 134 and then be processed by signal processor 132, A/D 33 and processor 150. Or multiple input channels consisting of additional sensors 120, multiplexer 134, amp 131, signal processor 132, A/D 133 could be multiplexed into processor 150. Those skilled in the art will obviously note other architectures.

The signal from A/D 133 is then input into a suitable processor 150. The processor may be one or more actual processors optimized for running various parts of the system. A coherent detection is then performed within the processor between the digitized signal and a suitably phase shifted version of the digitized waveforms that drove D/A 141. It should be appreciated that other signal extraction methods could be performed in place of or in addition to coherent detection, including FFTs, auto and cross-correlation, FIR and IIR filtering, etc. These signal processing methods can also be implemented outside the processor within signal processor 132. Processor 150 now determines the P&O of sensor 120. Processor 150 controls signal generation and detection, multiplexing and I/O with other systems.

The functional diagram shown in FIG. 14 illustrates the preferred 6DOF embodiment when lower accuracy is acceptable. It is similar to the preferred embodiment illustrated in FIG. 13 with the exception that only 2 generating coils are required. The components of this embodiment are given the same numbers as the corresponding components of FIG. 13.

System Parameter Determination

The equations presented so far have been in terms of known parameters $\lambda_p$, $\lambda_q$, $I_p$, $a_p$, k, r (the distance between the center of each sensor coil and the point x, y, z in equations 24–31 and 43–54), and rotation matrices. These parameters need to be determined accurately before any P&O process is implemented. $I_p$ can be determined within the tracking system via specific measurement circuitry. The other parameters can be determined by running the P&O process in reverse.

Specifically, if a sensor with known parameters (obtained by other means) is placed at a multitude of known P&Os, then the other parameters can be solved for using a least squares approach. The starting point is based on mechanical measurements of the B-field generator coil positions and orientations and manufacturing specifications of both generating and sensing coils. The data is most easily collected with a mechanized x-y-z translation table that moves a mechanized gimbal, such as schematically shown in FIG. 15. The gimbal may have the sensing coils on it and the generating coils fixed nearby or vice versa. The gimbal is designed to allow the sensing device to be placed at various orientations. Of course, the table and gimbal must be more accurate than the parameters you are trying to determine. It is assumed that the P&O of the sensing device within the gimbal is always known. This allows one to calibrate the relation between the sensing and generating devices such that the measurements made later on actual patients will be highly accurate.

FIG. 16 shows a simplified block diagram of the quality of solution process used by the processors such as processor 50 of FIG. 11. Initially, a tracking system would be evaluated by measuring the norms within a specified volume, as noted in box 200. This would be performed as part of the manufacturing process in a distortion free environment. The norm measures the residual error remaining after a proposed P&O solution is plugged back into the defining equations and indicates how accurate the P&O solution is. The worst case norm would be noted for the system and shipped with the system. It would also be used to set a related threshold level as shown in box 202. Once the tracker is placed in use by a customer, all subsequent P&O solution norms calculated in box 204 would be compared to the threshold level. If the P&O solution norm exceeds the threshold level an indication would be made to the user signifying that the P&O solution is suspect, as shown in box 206. This process continues indefinitely, comparing each new solution norm to the threshold. This process thereby alerts the user to problems within the environment. Once the environmental problem is corrected the indicator is automatically reset by the tracking system. Alternately, the norms could be monitored over the volume of interest once the tracking system was placed in operation. This process would typically be done once the system was installed in its final tracking environment. This way the worst case norm represents the specifics of the users environment. In either case the introduction of distorters to the tracking environment would increase the norm above the threshold level, indicating that the solution is not as good as it once was.

FIG. 17 shows a simplified block diagram of a process used with the present invention in the compensation of magnetic field distortion caused by conductive materials. Assume that the norm is sufficiently small in a magnetically clean (no distortion) environment. Now the system is started at either a known P&O in the vicinity of distorters or in a region that is free of distorters as shown in block 210. If started at a known P&O, then the residuals making up the norm are a measure of the distortion. These values can be low pass filtered to eliminate noise impulses and provide short-term memory as shown in block 212. If starting in a region without distortion the residuals are already small. As distorters are now introduced the magnitude of the residuals will increase. The residuals can again be low pass filtered to eliminate noise impulses as noted in block 212. In either case the filtered residuals are subtracted from the defining equations as shown in block 214. The next computation cycle of P&O determination then uses the adjusted equations as noted in block 216. This process continues indefinitely.

Figure 18:
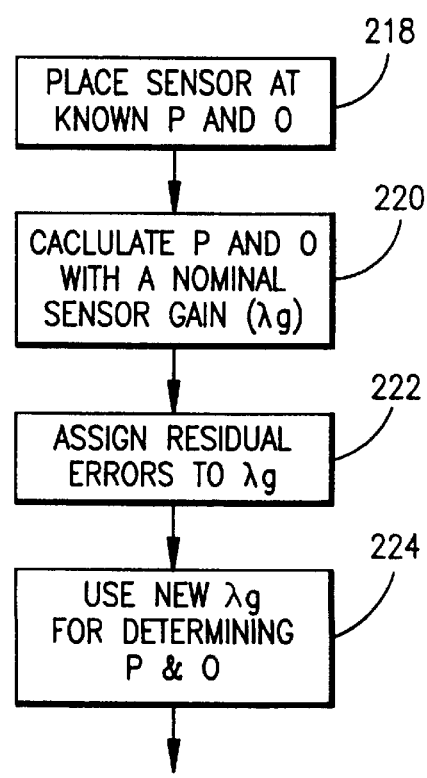
FIG. 18 is a flowchart on the use of a known starting point as a means of calibrating a coil in a catheter.

FIG. 18 shows a sensor calibration process that may be performed using any of the tracking systems of FIGS. 11–14. The assumption here is that the rest of the system has already been characterized using the apparatus shown in FIG. 15 and only the sensor needs calibration. An example of this would be when a new sensor is used with a calibrated tracking system. At block 218, the sensor is placed at a known position and orientation. This could be a special mount or reference point that is fixed in relation to the B-field generating coils. The P&O data is calculated at block 220 assuming a nominal sensor gain. At block 222, deviations between the known P&O and calculated P&O are assigned to errors from the sensor gain. A new sensor gain is established in block 224. Thus new sensor gain may then be used for actual patient measurements.

Disposable Sensor

Turning now to FIGS. 19–23, a specific type of disposable sensing coil that may be used with the present invention is discussed. The sensing coil 300 is disposable as that term is used in the medical field where certain medical items are designed with disposal in mind. These include items that cannot easily be sterilized and items that are not cost-effectively sterilized.

Figure 2:
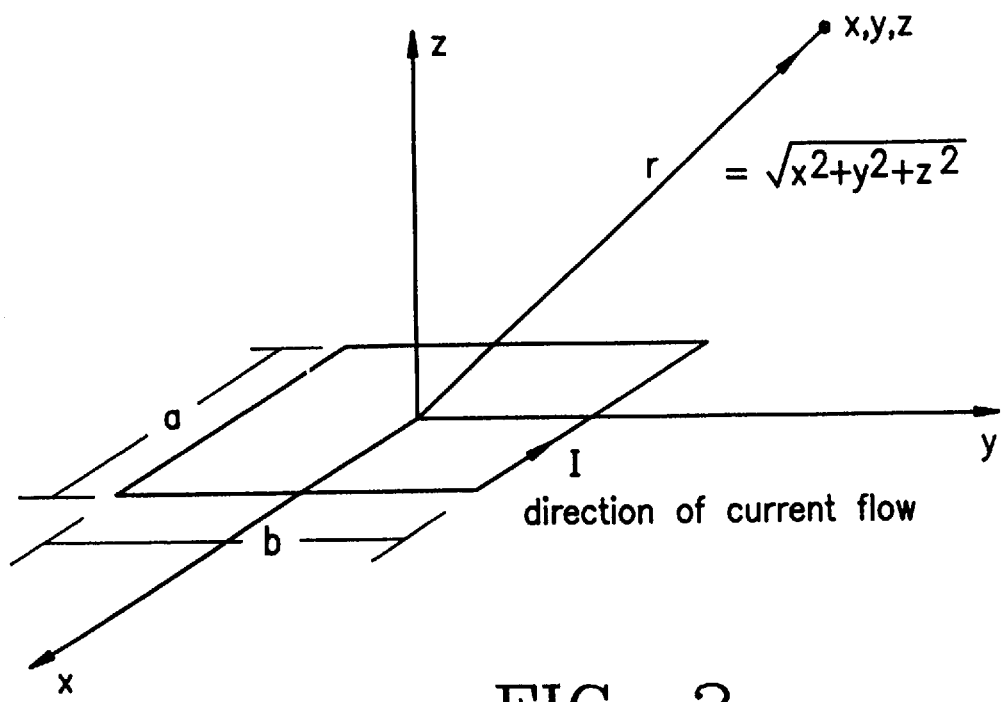
Figure 19:
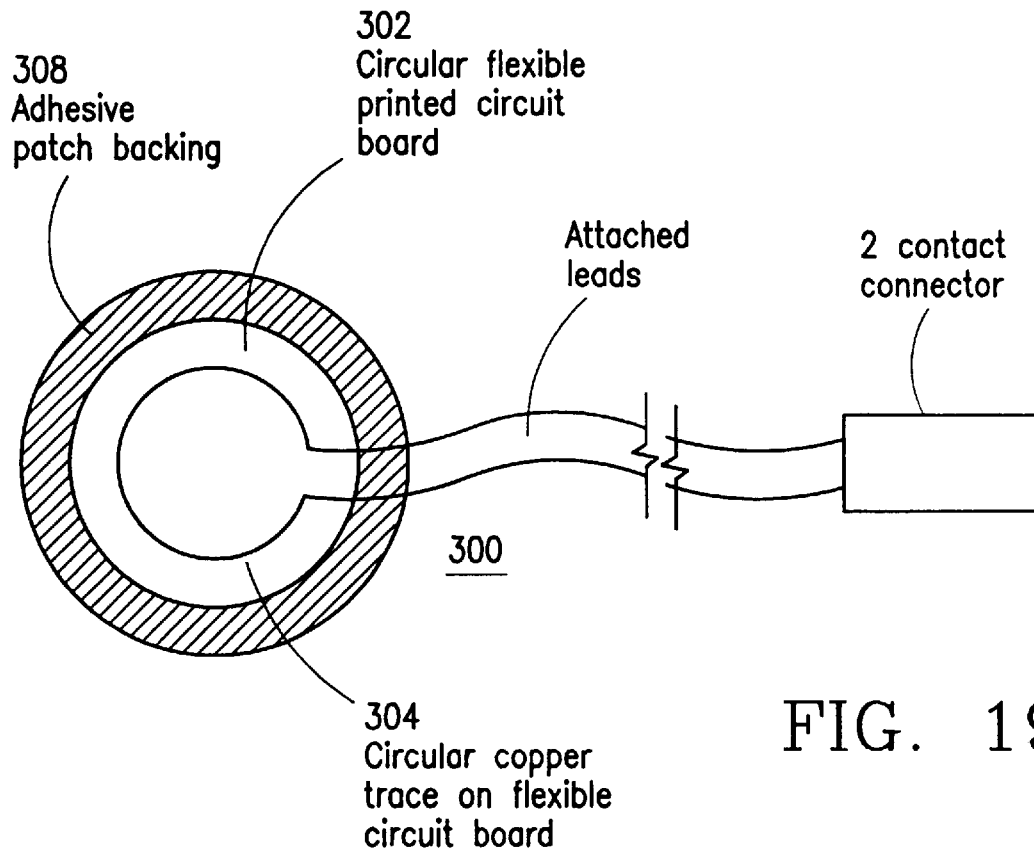
FIGS. 19–23 are simplified top views of various disposable sensors used with the present invention.
Figure 20:
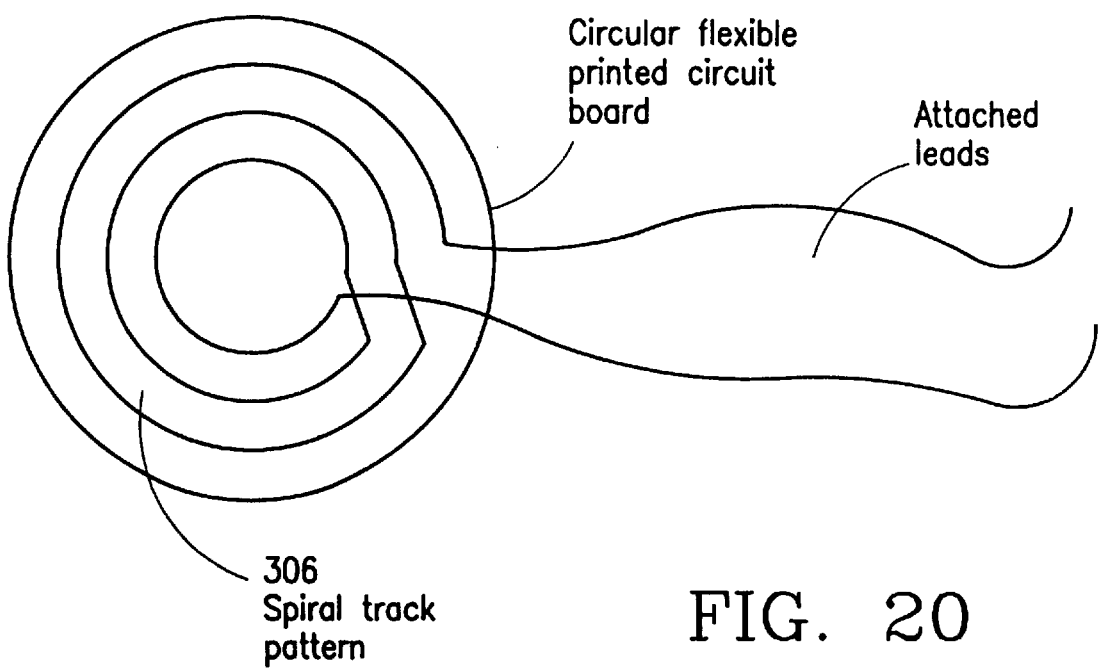

The 5DOF tracking implementation provides the ability to construct inexpensive sensing coils for tracking exterior portions of the body or exposed interior portions. A single sensing coil 300 can be built by laying out a flexible circuit board 302 composed only of a circular track pattern 304 (FIG. 19). Other patterns are possible including a spiral pattern 306 (FIG. 2). For all of the sensors discussed with reference to FIGS. 19–23, an adhesive patch backing 308 (shown in FIG. 19 only) is used to adhere the sensor to part of a patient. Leads would be integrally attached and terminated with a simple 2 contact connector (FIG. 19).

Figure 21:
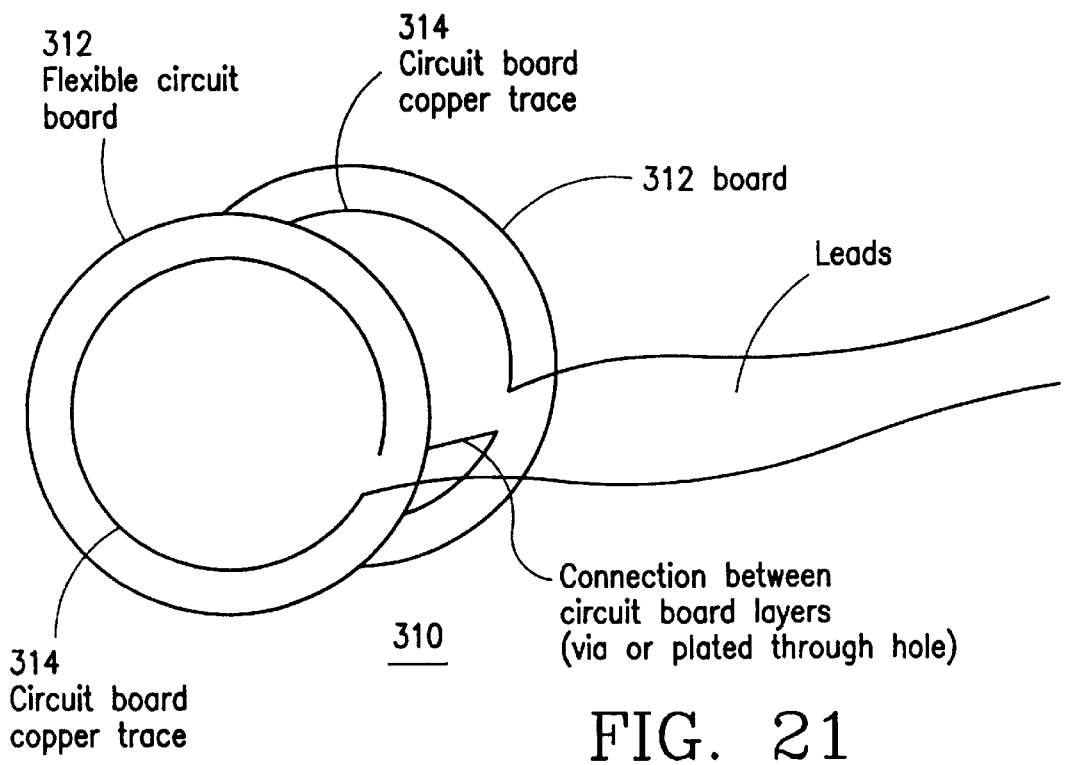

A multiple layered flexible circuit board 310 allows the coil pattern to be extended in the z direction (FIG. 21). Both of the aforementioned methods improve the coil sensitivity. The sensor board 310 has two boards 312 adhered together (shown offset for ease of illustration) and two copper trace coils 314.

Figure 22:
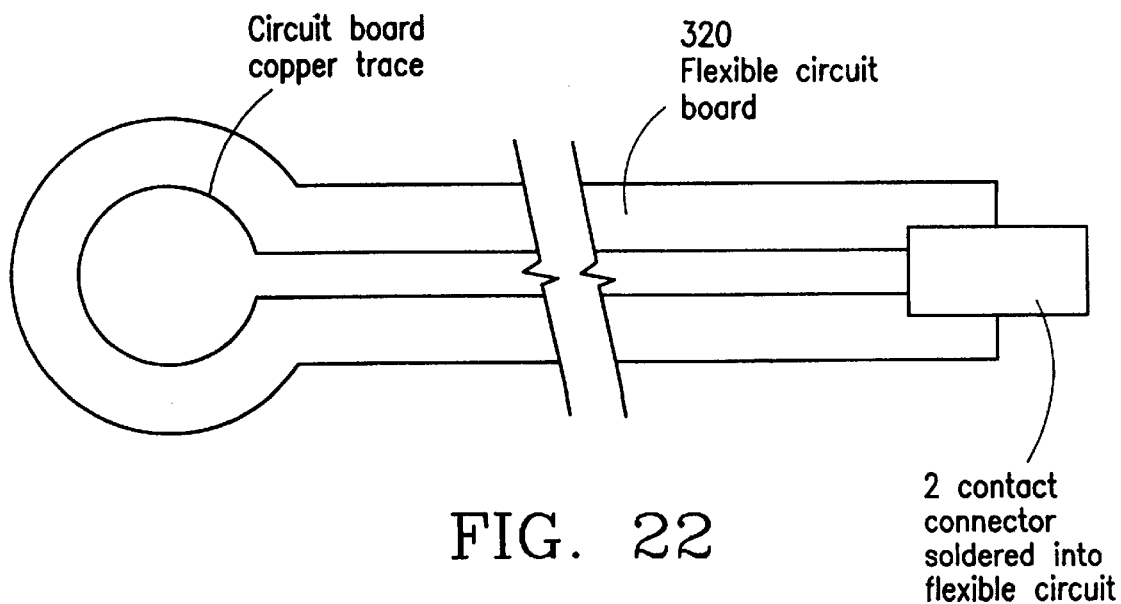
Figure 23:
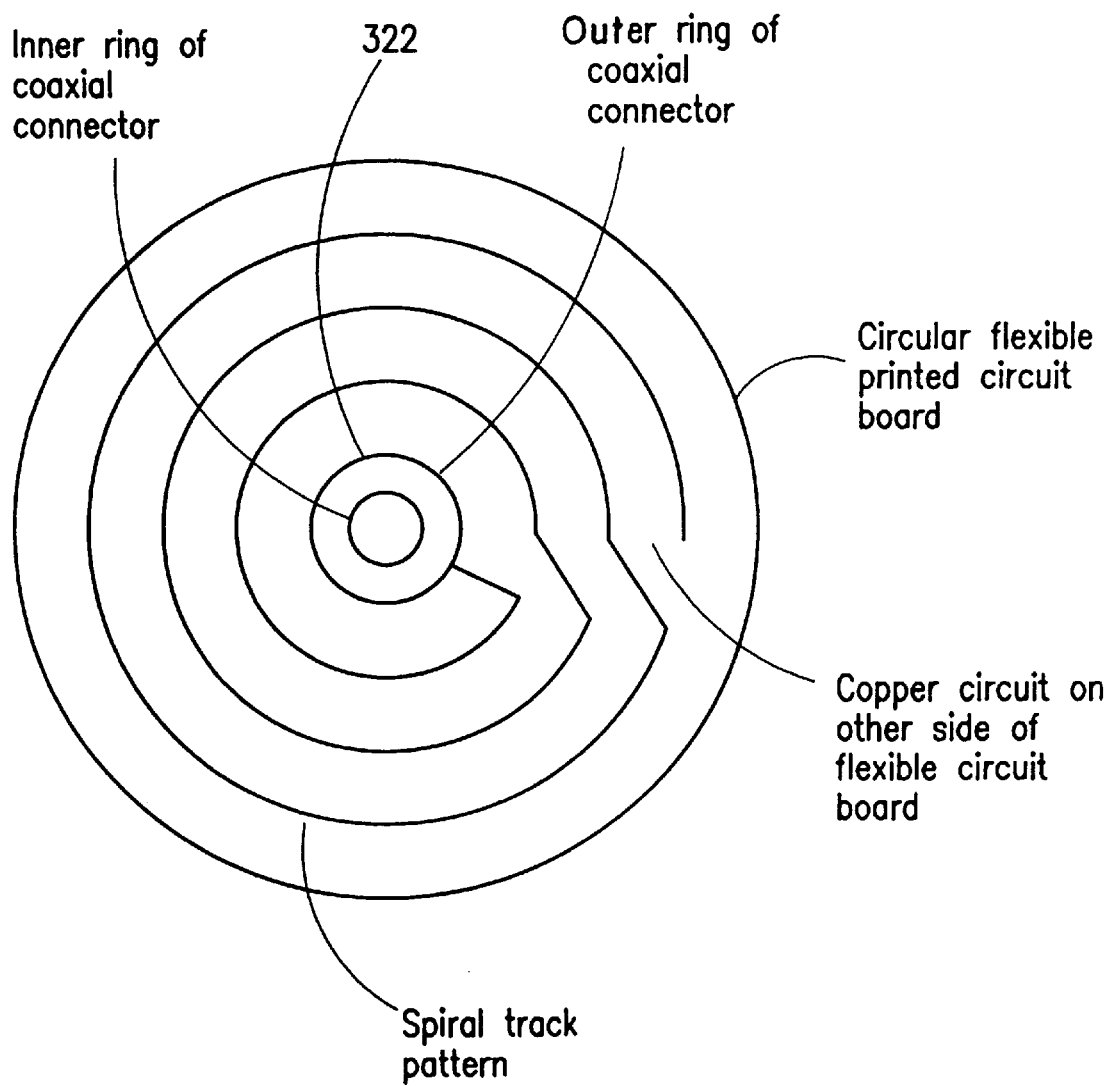

Another possibility is to use flexible circuit board material 320 for the leads too (FIG. 22). A further possibility would be to incorporate a concentric coaxial snap connector 322 onto the flexible circuit for quick connect/disconnect capabilities (FIG. 23).

The flexible circuit board is mounted to an adhesive patch (FIG. 19). Both items can be produced in a sterile environment and transported in a suitable sterile package.

Disposable Sensor Uses

The disposable sensor can be used in many of the same applications as a non-disposable and various sizes could be constructed for different applications. Gait analysis setup would be facilitated because you would just place the patches at the point you want to monitor and you would be done. Velcro straps, large elastic bandages and other cumbersome attachment methods are presently used. The alignment of joints in arthroplasty procedures could be drastically improved by measuring the position and orientation of bone alignment before and during the procedure. In this case a bone nail or pin could be pushed through the center of the disposable sensor and attached at a suitable point of reference.

Uses

The remote object position and orientation determining system of the present invention has a wide variety of applications. For example, sensor 20 can be placed at the end of a catheter or flexible endoscope for tracking the path of travel or the location of the catheter tip. This is especially useful in cardiac applications, e.g., for the treatment of cardiac arrhythmias, drug delivery and biopsy needle placement. Another use for sensor 20 is to embed the sensor into a contact lens for eye tracking. The eye tracking could also facilitate laser eye surgery by adjusting the aim of the laser during eye movements. Another application would place numerous sensor 20s around the fingers to provide a measure of finger movement for evaluating rehabilitation progress or as part of a virtual reality data glove, a device that allow hand movement to be translated into a virtual environment. Another application of sensor 20 would be to align prostheses during arthroplasty procedures. Sensor 20 can also be associated with the stylus of a three dimensional digitizer which is used to trace a physical model or the like and generate a digital database. The resulting database can then be used to generate a wide variety of computer generated images of the physical model. It should also be obvious that a 2 dimensional digitizer can be constructed using this technology. Still another application would be as a stylus input for a Personal Digital Assistant (PDA).

Sensor 120 can be used for forming three dimensional echocardiograms by tracking a handheld ultrasound scanner head. In still another application, sensor 120 can be associated with a particular body part for the purpose of conducting biomechanical studies. Still another application involves the monitoring of the body movements of an invalid for the purpose of creating a nonverbal communication system or providing a technique for remotely controlling various devices with nonverbal communicative body motion. Still another application is the production of data gloves, devices that allow hand movement to be translated into a virtual environment. Another application is the tracking of head movements for use in virtual reality headsets. Still another application is a 3 dimensional mouse for navigating in multidimensional databases or as a tool for use with VRML, a 3 dimensional file format popular on the Internet.

Following is a list of documents providing mathematical and related background discussion and as referred to above by number:

(1) Dennis Jr., J. E., Schnabel, Robert B. "Numerical Methods for Unconstrained Optimization and Nonlinear Equations." Prentice-Hall, Inc., 1983.
(2) More, Jorge J., Garbow, Burton S., Hillstrom, Kenneth E. "User Guide For MINPACK-1." Argonne National Laboratory, August 1980.
(3) Dennis Jr., John E., Gay, David M., Welsch, Roy E. "ALGORITHM 573, NL2SOL-An Adaptive Nonlinear Least-Squares Algorithm." ACM Transactions on Mathematical Software, Vol. 7, No. 3, September 1981, pages 369–383.
(4) More, Jorge J., Cosnard, Michel Y. "ALGORITHM 554, BRENTM, A Fortran Subroutine for the Numerical Solution of Systems of Nonlinear Equations." ACM Transactions on Mathematical Software, Vol. 6, No. 2, June 1980, pages 240–251.
(5) Schnabel, Robert B., Frank, Paul D. "Tensor Methods for Nonlinear Equations." SIAM Journal on Numerical Analysis, Vol. 21 No. 5, October 1984, pages 815–843.
(6) Aird, Thomas J., Rice, John R. "Systematic Search in High Dimensional Sets." SIAM Journal on Numerical Analysis, Vol. 14 No. 2, April 1977 1984, pages 296–312.
(7) Aluffi-Pentini, Filippo, Parisi, Valerio, Zirilli, Francesco. "ALGORITHM 617, DAFNE: A Differential-Equations Algorithm for Nonlinear Equations." ACM Transactions on Mathematical Software, Vol. 10, No. 3, September 1984, pages 317–324.
(8) Aluffi-Pentini, Filippo, Parisi, Valerio, Zirilli, Francesco. "ALGORITHM 667, SIGMA: A Stochastic-Integration Global Minimization Algorithm." ACM Transactions on Mathematical Software, Vol. 14, No. 4, December 1988, pages 366–380.
(9) Vrahatis, Michael N. "Solving Systems of Nonlinear Equations Using the Nonzero Value of the Topological Degree." ACM Transactions on Mathematical Software, Vol. 14, No. 4, December 1988, pages 312–329.
(10) Kearfott, R. Baker, "Interval Arithmetic Techniques in the Computational Solution of Nonlinear Systems of Equations: Introduction, Examples, and Comparisons." Lectures in Applied Mathematics, American Mathematical Society, Vol. 26, 1990.
(11) Press, William H., Teukolsky, Saul A., Vetterling, William T., Flannery, Brian P. "Numerical Recipes in FORTRAN, The Art of Scientific Computing, Second Edition." Cambridge University Press, 1992.
(12) Brown, Kenneth M. "Computer Oriented Algorithms for Solving Systems of Simultaneous Nonlinear Algebraic Equations," in Numerical Solution of Systems of Nonlinear Algebraic Equations, Academic Press, 1973, pages 281–348.
(13) Scarf, H., "The Approximation of Fixed Points of a Continuous Mapping," SIAM Journal Applied Mathematics, Vol. 15, 1967, pages 1328–1343.
(14) Schwefel, Hans-Paul, "Numerical Optimization of Computer Models." John Wiley & Sons, Ltd., 1981.

Although specific constructions have been presented herein, it is to be understood that these are for illustrative purposes only. Various modifications and adaptations will be apparent to those of skill in the art. In view of possible modifications, it will be appreciated that the scope of the present invention should be determined by reference to the claims appended hereto.

What is claimed is:

1. A medical system for treating a patient comprising:
a plurality of transducers operable to determine the location of a medical device in a patient, the transducers are electromagnetic and include one or more device transducers and one or more external transducers; a medical device for insertion into a patient, the medical device having the one or more device transducers;
an external locator operable outside and adjacent to the patient, the external locator having the one or more external transducers;
a driver connected to sequentially energize one or more of the device transducers and/or the external transducers;
a processor operably connected to receive sensor signals from one or more of the transducers, each sensor signal on a given one of the transducers depending on the energizing of another of the transducers, the processor configured to iteratively determine at least two location parameters of the medical device in a patient using a plurality of equations that remain valid for zero separation distance from the energized transducer to the transducer generating the sensor signal for validity.

2. The medical system of claim 1 wherein the medical device is a catheter.

3. The medical system of claim 2 wherein the catheter is a laser catheter operable for endomyocardial revascularization.

4. The medical system of claim 3 wherein each of the transducers is operable to generate and/or sense an electromagnetic field.

5. The medical system of claim 4 wherein the processor determines n location parameters of the laser catheter and the number of transducers is less than n.

6. The medical system of claim 4 wherein there is only one device transducer and there are a plurality of external transducers.

7. The medical system of claim 2 wherein the processor is configured to determine n location parameters of the catheter and the number of transducers is less than n.

8. The medical system of claim 1 wherein the processor is configured to determine n location parameters of the medical device and the number of transducers is less than n.

9. A system for determining the location of a remote device comprising:
a plurality of transducers operable to determine the location of a remote device in an operation zone, the transducers are electromagnetic and include one or more device transducers and one or more locator transducers;
a remote device for placement in an operation zone, the remote device having the one or more device transducers; a locator operable away from, but within an interaction distance from, the remote device, the locator having the one or more locator transducers;
a driver connected to sequentially energize one or more of the device transducers and/or the locator transducers;
a processor operably connected to receive sensor signals from one or more of the transducers, each sensor signal on a given one of the transducers depending on the energizing of another of the transducers, the processor configured to iteratively determine at least two location parameters of the remote device in the patient using a plurality of equations of exact magnetic field coupling that remain valid for zero separation distance from the energized transducer to the transducer generating the sensor signal for validity; and wherein each of the transducers generates and/or senses an electromagnetic field.

10. The system of claim 9 wherein the system is a medical system, the remote device is a medical device and the operation zone is within a patient.

11. The system of claim 10 wherein the medical device is a laser catheter operable for endomyocardial revascularization.

12. The system of claim 11 wherein the processor determines n location parameters of the laser catheter and the number of transducers is less than n.

13. The system of claim 12 wherein n is at least five.

14. The system of claim 10 wherein there is only one device transducer and there are a plurality of locator transducers.

15. The system of claim 9 wherein there is only one device transducer and there are a plurality of locator transducers.

16. The system of claim 9 wherein the locator transducers generate electromagnetic fields and each device transducer senses the electromagnetic fields.

17. The system of claim 9 wherein the processor is configured to determine n location parameters of the remote device and the number of transducers is less than n.

18. The system of claim 17 wherein n is at least five.

19. A method of determining the location of a remote device comprising the steps of:

using a system having a plurality of coils operable to determine the location of a remote device, the coils including one or more device coils and one or more locator coils;

placing the remote device in an operation zone, the remote device having the one or more device coils;

placing a locator away from, but within an interaction distance from, the remote device, the locator having the one or more locator coils;

sequentially energizing one or more of the device coils and/or the locator coils;

generating sensor signals from one or more of the coils, each sensor signal on a given one of the coils depending on the energizing of another of the coils;

supplying the sensor signals to a processor; and determining by operation of the processor at least two location parameters of the remote device using a plurality of equations that remain valid for zero separation distance from the energized coil to the coil generating the sensor signal for validity; and wherein the system is a medical system used to treat a patient, the remote device is a medical device and the operation zone is within a patient.

20. The method of claim 19 wherein the step of sequentially energizing one or more of the device coils and/or the locator coils causes each energized coil to generate an electromagnetic field.

21. The method of claim 19 wherein the determining step determines a number N of locator parameters and there are N-1 coils.

22. The method of claim 19 wherein the step of placing the medical device includes placing a catheter in a patient.

23. The method of claim 19 wherein the step of placing the medical device includes placing a catheter in a patient.

24. The method of claim 23 further comprising the steps of:

positioning the laser catheter within the heart of a patient using the determined location parameters to move the laser catheter to a desired location; and lasing from the laser catheter so as to perform endomyocardial revascularization.

25. A method of determining the location of a remote device comprising the steps of:

using a system having a plurality of coils operable to determine the location of a remote device, the electromagnetic transducers including one or more device electromagnetic transducers and one or more locator electromagnetic transducers;

placing the remote device in an operation zone, the remote device having the one or more device electromagnetic transducers;

placing a locator away from, but within an interaction distance from, the remote device, the locator having the one or more locator electromagnetic transducers;

sequentially energizing one or more of the device electromagnetic transducers and/or the locator electromagnetic transducers;

generating sensor signals from one or more of the electromagnetic transducers, each sensor signal on a given one of the electromagnetic transducers depending on the energizing of another of the electromagnetic transducers; and supplying the sensor signals to a processor, the processor determining at least two location parameters of the remote device using a plurality of equations that remain valid for zero separation distance from the energized transducers to the transducers generating the sensor signal for validity; and wherein each of the electromagnetic transducers generates and/or senses an electromagnetic field.

26. The method of claim 25 wherein steps of energizing and generating sensor signals use electromagnetic transducers selected from the group consisting of: coils, Hall-effect sensors, magnetometers, magnetoresistive devices, magnetoinductive devices, and galvanomagnetic devices.

27. The method of claim 25 wherein the using a system step is specifically using a medical system to treat a patient, and wherein the step of placing the remote device in an operation zone is specifically placing a medical device within a patient.

28. The method of claim 25 wherein the processor determines the at least two location parameters of the remote device by checking to insure that residual errors are less than a given threshold.

29. The method of claim 25 wherein the processor determines the at least two location parameters of the remote device by taking into account previously determined distortions.

30. The method of claim 29 further including the steps of, prior to the placement of the remote device in an operation zone, placing the remote device in a known position relative to the locator, determining the deviation between sensed position data and known position data, and adjusting for distortions based on the deviations such that the at least two location parameters of the remote device by take into account distortions.

* * * * *